United States Patent [19]

Sarthy et al.

[11] Patent Number: 6,022,712

[45] Date of Patent: *Feb. 8, 2000

[54] ENHANCED YEAST EXPRESSION USING REGULATORY CONTROL SEQUENCES FROM YEAST SORBITOL DEHYDROGENASE GENE

[75] Inventors: Aparna V. Sarthy, Waukegan, Ill.; Cynthia W. Schopp, Gig Harbor, Wash.

[73] Assignee: Abbott Laboratories, Abbott Park, Ill.

[ * ] Notice: This patent is subject to a terminal disclaimer.

[21] Appl. No.: 08/466,548

[22] Filed: Jun. 6, 1995

Related U.S. Application Data

[62] Division of application No. 07/998,226, Dec. 30, 1992.

[51] Int. Cl.$^7$ .............................. C12P 21/00; C12P 21/02; C12N 1/19; C12N 15/81
[52] U.S. Cl. .................... 435/69.7; 435/69.1; 435/320.1; 435/483
[58] Field of Search ................................ 435/69.1, 320.1, 435/172.3, 69.7, 483

[56] References Cited

U.S. PATENT DOCUMENTS

| | | | |
|---|---|---|---|
| 4,966,841 | 10/1990 | Riley | 435/69.1 |
| 4,977,092 | 12/1990 | Bitter | 435/320.1 |
| 5,089,398 | 2/1992 | Rosenberg et al. | 435/69.1 |
| 5,116,750 | 5/1992 | Gelfand et al. | 435/193 |
| 5,139,936 | 8/1992 | Botstein et al. | 435/69.1 |

OTHER PUBLICATIONS

Snyder et al., Methods in Enzymology 154:107–128 (1987).
Jörnvall et al., Eur. J. Biochem. 140:17–23 (1984).

*Primary Examiner*—Johnny F. Railey, II
*Attorney, Agent, or Firm*—Dianne Casuto

[57] ABSTRACT

An isolated DNA segment is disclosed which is derived from a *Saccharomyces cerevisiae* sorbitol dehydrogenase gene and which functions to increase expression of an associated foreign polypeptide when the DNA segment and the gene coding for the foreign polypeptide are operably linked in a vector in such a manner that the vector is replicated and carried by a host yeast cell. The functionally active portion of the segment is under the control (i) a transcriptional regulatory sequence of the sorbitol dehydrogenase gene of *Saccharomyces cerevisiae*, (ii) a translation initiation regulatory sequence of the sorbitol dehydrogenase gene of *Saccharomyces cerevisiae*, and (iii) a termination regulatory sequence of the sorbitol dehydrogenase gene of *Saccharomyces cerevisiae*. Yeast cells containing these regulatory sequences linked to a foreign DNA sequence are grown in medium containing sorbitol under conditions permitting a foreign polypeptide to be expressed.

4 Claims, 17 Drawing Sheets

```
1    AAGCTTAGTTTATCAATTTTTGTGAAACTTTGACTAATGACGTATTATTGTGGTGTGC    60
     ----+----+----+----+----+----+----+----+----+----+----+----+

61   ATTACGACCAAAAGGCGGGCTAACAATTCCAAGGAAAAAAGCTGGTGTAAACCTGACTGT   120
     ----+----+----+----+----+----+----+----+----+----+----+----+

121  TTGCCACGGCTTTTCTTACTACTAAATCGGTAGCAGGCATGAAGGAATCGTGAATGGTGT   180
     ----+----+----+----+----+----+----+----+----+----+----+----+

181  GACCTGAGACAAGGAGAGGCAGGCATGAAGGCAAACAAATTACGGGGAAGGCACAGGAG    240
     ----+----+----+----+----+----+----+----+----+----+----+----+

241  ATACCCCCACTAAAGATTACCCCACAATCCCTTATTTTCTCGAGCTCCCTGCAGGAGAGT   300
     ----+----+----+----+----+----+----+----+----+----+----+----+

301  AAGTTTTAGGCACATATAGTGCAGAAAATAAAGTTTTCGCGACAGCTACTGCCGAGTG    360
     ----+----+----+----+----+----+----+----+----+----+----+----+

361  GCAAAATCTATGTTGAAGTTGGAAAGTTACGCCCTAGCTTCAGGAACCATCGGGCTTGTT   420
     ----+----+----+----+----+----+----+----+----+----+----+----+

421  GGGGTGAATAATGAAGGAACTTCGTTCAGAAAACTGTTGTCTTTACCAAGCACTTTAATG   480
     ----+----+----+----+----+----+----+----+----+----+----+----+
```

FIG. 1A

```
481  CTTTCTTCCTCTCTTCAACAGTTAAGTTCATCATATATTCTATTATCTCCGGTCTCGTATCTC  540

541  CTTTCTCCGGTCACATGAAGCCTCTGTATCACCTTGCTAACCGCATTTCTTCCATCTAAA  600

601  GTATGTTCATTGCCATAAGTGCTTACTCTCTCTTTAATATATAGAAAAAATTCGACAT  660

661  ATAAAAGGCTCAATGTCTTACCGTTCATCTTTATGAAGAGATATAGTATAAGTGGAAAAA  720

721  AGAAACATCAAACAATCAACAAGAAAAAATACTAAAAAAAAATTGAAAAATATGTCTC  780
                                                              fM  S  Q

781  AAAATAGTAACCCTGCAGTAGTTCTAGAGAAAGTCGGCGATATTGCCATCGAGCAAAGAC  840
      N  S  N  P  A  V  V  L  E  K  V  G  D  I  A  I  E  Q  R_P

841  CAATCCCTACCATTAAGGACCCCCATTATGTCAAGTTAGCTATTAAAGCCACTGGTATCT  900
      I  P  T  I  K  D  P  H  Y  V  K  L  A  I  K  A  T  G  I  C
```

FIG.1B

```
 901 GCGGCTCTGATATTCATTATTATAGAAGCGGTGGTATTGGTAAGTACATATTGAAGGCGC  960
      G  S  D  I  H  Y  Y  R  S  G  G  I  G  K  Y  I  L  K  A  P

961 CAATGGTTTAGGTCATGAATCAAGCGGACAGGTTGTGGAAGTTGGTGATGCCGTCACAA 1020
      M  V  L  G  H  E  S  S  G  Q  V  V  E  V  G  D  A  V  T  R

1021 GGGTCAAAGTTGGTGACCGTGTTGCTATTGAACCTGGTGTTCCTAGCCGTTACTCTGATG 1080
      V  K  V  G  D  R  V  A  I  E  P  G  V  P  S  R  Y  S  D  E

1081 AGACCAAAGAAGGGAGGTATAAACCTTTGCCCACATATGGCATTTGCTGCAACTCCTCCAA 1140
      T  K  E  G  R  Y  N  L  C  P  H  M  A  F  A  A  T  P  P  I

1141 TTGATGGTACTCTTGTGAAGTACTATTATCTCCAGAAGATTTCCTTGTGAAATTGCCAG 1200
      D  G  T  L  V  K  Y  Y  L  S  P  E  D  F  L  V  K  L  P  E

1201 AAGGCGTCAGTTATGAAGAGGGCGCTTGTGTCGAACCCTTATCAGTCGGTGTACACTCTA 1260
      G  V  S  Y  E  E  G  A  C  V  E  P  L  S  V  G  V  H  S  N
```

FIG.1C

```
1261  ATAAATTGGCTGGGGTCCGCTTTGGTACCAAAGTTGTGTATTGGTGCAGGTCCTGTGG
      ----+----+----+----+----+----+----+----+----+----+----+----+ 1320
         K  L  A  G  V  R  F  G  T  K  V  V  V  F  G  A  G  P  V  G

1321  GGCTTTTAACTGGCGCAGTCGCCCGCGCTTTTGGTGCCACCGACGTCATTTCGTCGATG
      ----+----+----+----+----+----+----+----+----+----+----+----+ 1380
         L  L  T  G  A  V  A  R  A  F  G  A  T  D  V  I  F  V  D  V

1381  TATTCGACAACAAGCTACAGAGAGCAAAAGATTTCGGAGCCACAAACACTTTCAATTCTT
      ----+----+----+----+----+----+----+----+----+----+----+----+ 1440
         F  D  N  K  L  Q  R  A  K  D  F  G  A  T  N  T  F  N  S  S

1441  CCCAGTTTTCCACCGATAAAGCCCAAGACTTGGCCGATGGGGTCCAAAAGCTTTTGGGCG
      ----+----+----+----+----+----+----+----+----+----+----+----+ 1500
         Q  F  S  T  D  K  A  Q  D  L  A  D  G  V  Q  K  L  L  G  G

1501  GAAATCACGCAGATGTGTGTTTGAGTGTGTTCAGGTGCTGATGTTTGCATTGATGCCGCTG
      ----+----+----+----+----+----+----+----+----+----+----+----+ 1560
         N  H  A  D  V  V  F  E  C  S  G  A  D  V  C  I  D  A  A  V

1561  TCAAAACAACTAAGGTTGGAGTACCATGTGGTGCAAGTCGGTATGGGTAAAAACTACACTA
      ----+----+----+----+----+----+----+----+----+----+----+----+ 1620
         K  T  T  K  V  G  G  T  M  V  Q  V  G  M  G  K  N  Y  T  N
```

FIG. 1D

```
1621  ATTTCCAATTGCTGAAGTTAGTGGAAAGGAAATGAAATTGATTGGATGTTTCCGTTATT  1680
       ------+---------+---------+---------+---------+---------+
        F  P  I  A  E  V  S  G  K  E  M  K  L  I  G  C  F  R  Y  S

1681  CATTCGGTGATTATCGTGACGCTGTGAACTTGGTTGCCACAGGAAAAGTCAATGTCAAGC  1740
       ------+---------+---------+---------+---------+---------+
        F  G  D  Y  R  D  A  V  N  L  V  A  T  G  K  V  N  V  K  P

1741  CATTGATAACCCACAAATTTAAATTTGAAGATGCAGCCAAGGCTTACGACTACAACATTG  1800
       ------+---------+---------+---------+---------+---------+
        L  I  T  H  K  F  K  F  E  D  A  A  K  A  Y  D  Y  N  I  A

1801  CCCATGGTGGAGAGGTAGTCAAGACTATTATCTTTGGTCCTGAATGAAAAGTGAATACTT  1860
       ------+---------+---------+---------+---------+---------+
        H  G  G  E  V  V  K  T  I  I  F  G  P  E  *

1861  TTCGGCACTGGTTCATGTCCATATATAGACCAATTCAAAAGCAGTAATACTTGAAAAT  1920
       ------+---------+---------+---------+---------+---------+

1921  AACACCGAAAAATAAAAAATTTAAATAGTAGACACGTTTAAATGACTTAAAAACTAACTTTT  1980
       ------+---------+---------+---------+---------+---------+

1981  TCATATCTAATATTGTAAAATGGGCGAAAAAGCTTAAGAATATGTTATTTACAAATCA  2040
       ------+---------+---------+---------+---------+---------+
```

FIG.1E

```
2041 GAGCGGCTGACACATATAGAGAGCTATATGATGAGTGAGAGCAACTCTCCCGTATATGC
     ----------+---------+---------+---------+---------+---------+  2100

2101 TAAGAATATTGTCGCTTATTAGGATTGAAAGATAGGATCAATGAGGAATAAATGTTACCC
     ----------+---------+---------+---------+---------+---------+  2160

2161 TTTTTCTTAAAAATGTAAGAGGAAATTATGAAATATACTCTGATTTGTTTATTATTGAT
     ----------+---------+---------+---------+---------+---------+  2220

2221 TAAGAACAATATAATAACCGCTCTGGTAGCTACTGTACATATAATTTGACGGCATATATT
     ----------+---------+---------+---------+---------+---------+  2280

2281 GCTCATATATAAAACTACCGCATTACTTCCAGTTGATAGATTTTAACTCAGTTTCAGTA
     ----------+---------+---------+---------+---------+---------+  2340

2341 CTGCCCAGAACTGCTCATTCGAGATTTTTCTATTTTAGAATAGGTAAAATTGCACTTAA
     ----------+---------+---------+---------+---------+---------+  2400

2401 ATGTATAAGGGATGTACGAAGTGAGTGCCCAGACTGTTACTATGACAATTAAACTAAATGT
     ----------+---------+---------+---------+---------+---------+  2460

2461 CGATGACCATTTGTTTCGACAACTCCATCTTCATTTTCTTCACGGCCATACTCGGATGA
     ----------+---------+---------+---------+---------+---------+  2520
```

FIG. 1F

```
2521 GAAAGAATCTTTCTCTAACTATACATTTCCAAACGCAATGATCAAGAAGAAAGCTAAAT 2580
2581 GTTACTTTGAGTTCAATTACTGAGACATGTCATGGAATATGAGGAAGAAACAAATCTAC 2640
2641 GTGTATTATACTCCGTAACATGTAGAGTAAATACCATAGTTACCTATTTACCTGTGTCGA 2700
2701 TAAATGTTCATTAGCTTCATAAGTGATGGGATACATTGCTATTCCTCTGCAATGGAAGCTT 2760
```

FIG. 1G

Construction of pXS3, pXS4, pXS4 linker

Multi Cloning Site and Terminator:
5'AAT ATT ACC ATG GAT CCC CGG GGT CGA CTG AAT AAA TGA GTC GCGA SEQ ID No.:9
3'
   SspI   NcoI        SmaI   SalI   Terminator   NruI
         BamHI

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 2774 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: SACCHAROMYCES CEREVISIAE
        (B) STRAIN: 800B (ix) FEATURE:
        (A) NAME/KEY: CDS
        (B) LOCATION: 788..1856

(xi) SEQUENCE DESCRIPTION: SEQ ID NO:1:

```
ATCCCTTTAT TGATAAGCTT AGTTTATCAA TTTTTTGTGA AAACTTTGAC TAATGACGTA      60

TTATTGTGGT GTGCATTACG ACCAAAAGGC GGGCTAACAA TTCCAAGGAA AAAAGCTGGT     120

GTAAACCTGA CTGTTTGCCA CGGCTTTTCT TACTACTAAA TCGGTAGCAG GCATGAAGGA     180

ATCGTGAATG GTGTGACCTG AGACAAGGAG AGGCAGGCAT GAAGGCAAAC AAATTACGGG     240

GGAAGGCACA GGAGATACCC CCACTAAAGA TTACCCCACA ATCCCTTATT TTCTCGAGCT     300

CCCTGCAGGA GAGTAAGTTT TAGGCACATA TAGGTGCAGA AAATAAAGTT TTCGCGGACA     360

GCTACTGCCG AGTGGCAAAA TCTATGTTGA AGTTGGAAAG TTACGCCTAG CTTCAGGAAC     420

CATCGGGCTT GGTTGGGGTG AATAATGAAG GAACTTCGTT CAGAAAACTG TTGTCTTTAC     480

CAAGCACTTT AATGCTTTCT TCCTCTTCAA CAGTTAAGGT TCATCATATT CTATTATCTC     540

CGGTCTCGTA TCTCCTTTCT CCGGTCACAT GAAGCCTCTG TATCACCTTG CTAACCGCAT     600

TTCTTCCATC TAAAGTATGT TCATTGCCAT AAGTTGCTTA CTCTCTCTTT AATATATAGA     660

AAAAAATTCG ACATATAAAA GGCTCAATGT CTTACCGTTC ATCTTTATGA AGAGATATAG     720

TATAAGTGGA AAAAGAAAC ATCAAACAAT CAACAAGAAA AATACTAAA AAAAAAATT       780

GAAAAAT ATG TCT CAA AAT AGT AAC CCT GCA GTA GTT CTA GAG AAA GTC       829
        Met Ser Gln Asn Ser Asn Pro Ala Val Val Leu Glu Lys Val
        1               5                   10

GGC GAT ATT GCC ATC GAG CAA AGA CCA ATC CCT ACC ATT AAG GAC CCC       877
Gly Asp Ile Ala Ile Glu Gln Arg Pro Ile Pro Thr Ile Lys Asp Pro
15                  20                  25                  30

CAT TAT GTC AAG TTA GCT ATT AAA GCC ACT GGT ATC TGC GGC TCT GAT       925
His Tyr Val Lys Leu Ala Ile Lys Ala Thr Gly Ile Cys Gly Ser Asp
                35                  40                  45

ATT CAT TAT TAT AGA AGC GGT GGT ATT GGT AAG TAC ATA TTG AAG GCG       973
Ile His Tyr Tyr Arg Ser Gly Gly Ile Gly Lys Tyr Ile Leu Lys Ala
            50                  55                  60

CCA ATG GTT TTA GGT CAT GAA TCA AGC GGA CAG GTT GTG GAA GTT GGT      1021
Pro Met Val Leu Gly His Glu Ser Ser Gly Gln Val Val Glu Val Gly
        65                  70                  75

GAT GCC GTC ACA AGG GTC AAA GTT GGT GAC CGT GTT GCT ATT GAA CCT      1069
Asp Ala Val Thr Arg Val Lys Val Gly Asp Arg Val Ala Ile Glu Pro
    80                  85                  90

GGT GTT CCT AGC CGT TAC TCT GAT GAG ACC AAA GAA GGG AGG TAT ACC      1117
Gly Val Pro Ser Arg Tyr Ser Asp Glu Thr Lys Glu Gly Arg Tyr Asn
95                  100                 105                 110

CTT TGC CCA CAT ATG GCA TTT GCT GCA ACT CCT CCA ATT GAT GGT ACT      1165
Leu Cys Pro His Met Ala Phe Ala Ala Thr Pro Pro Ile Asp Gly Thr
```

```
                    115                 120                 125
CTT GTG AAG TAC TAT TTA TCT CCA GAA GAT TTC CTT GTG AAA TTG CCA    1213
Leu Val Lys Tyr Tyr Leu Ser Pro Glu Asp Phe Leu Val Lys Leu Pro
            130                 135                 140

GAA GGC GTC AGT TAT GAA GAG GGC GCT TGT GTC GAA CCC TTA TCA GTC    1261
Glu Gly Val Ser Tyr Glu Glu Gly Ala Cys Val Glu Pro Leu Ser Val
            145                 150                 155

GGT GTA CAC TCT AAT AAA TTG GCT GGG GTC CGC TTT GGT ACC AAA GTT    1309
Gly Val His Ser Asn Lys Leu Ala Gly Val Arg Phe Gly Thr Lys Val
            160                 165                 170

GTT GTA TTT GGT GCA GGT CCT GTG GGG CTT TTA ACT GGC GCA GTC GCC    1357
Val Val Phe Gly Ala Gly Pro Val Gly Leu Leu Thr Gly Ala Val Ala
175             180                 185                 190

CGC GCT TTT GGT GCC ACC GAC GTC ATT TTC GTC GAT GTA TTC GAC AAC    1405
Arg Ala Phe Gly Ala Thr Asp Val Ile Phe Val Asp Val Phe Asp Asn
                195                 200                 205

AAG CTA CAG AGA GCA AAA GAT TTC GGA GCC ACA AAC ACT TTC AAT TCT    1453
Lys Leu Gln Arg Ala Lys Asp Phe Gly Ala Thr Asn Thr Phe Asn Ser
            210                 215                 220

TCC CAG TTT TCC ACC GAT AAA GCC CAA GAC TTG GCC GAT GGG GTC CAA    1501
Ser Gln Phe Ser Thr Asp Lys Ala Gln Asp Leu Ala Asp Gly Val Gln
            225                 230                 235

AAG CTT TTG GGC GGA AAT CAC GCA GAT GTG GTG TTT GAG TGT TCA GGT    1549
Lys Leu Leu Gly Gly Asn His Ala Asp Val Val Phe Glu Cys Ser Gly
            240                 245                 250

GCT GAT GTT TGC ATT GAT GCC GCT GTC AAA ACA ACT AAG GTT GGA GGT    1597
Ala Asp Val Cys Ile Asp Ala Ala Val Lys Thr Thr Lys Val Gly Gly
255             260                 265                 270

ACC ATG GTG CAA GTC GGT ATG GGT AAA AAC TAC ACT AAT TTT CCA ATT    1645
Thr Met Val Gln Val Gly Met Gly Lys Asn Tyr Thr Asn Phe Pro Ile
            275                 280                 285

GCT GAA GTT AGT GGA AAG GAA ATG AAA TTG ATT GGA TGT TTC CGT TAT    1693
Ala Glu Val Ser Gly Lys Glu Met Lys Leu Ile Gly Cys Phe Arg Tyr
            290                 295                 300

TCA TTC GGT GAT TAT CGT GAC GCT GTG AAC TTG GTT GCC ACA GGA AAA    1741
Ser Phe Gly Asp Tyr Arg Asp Ala Val Asn Leu Val Ala Thr Gly Lys
            305                 310                 315

GTC AAT GTC AAG CCA TTG ATA ACC CAC AAA TTT AAA TTT GAA GAT GCA    1789
Val Asn Val Lys Pro Leu Ile Thr His Lys Phe Lys Phe Glu Asp Ala
            320                 325                 330

GCC AAG GCT TAC GAC TAC AAC ATT GCC CAT GGT GGA GAG GTA GTC AAG    1837
Ala Lys Ala Tyr Asp Tyr Asn Ile Ala His Gly Gly Glu Val Val Lys
355             340                 345                 350

ACT ATT ATC TTT GGT CCT G AATGAAAAGT GAATACTTTT CGGCACTGGT         1886
Thr Ile Ile Phe Gly Pro
            355

TCATGTCCAT ATATATAGAC CAATTCAAAA GCAGTAATAC TTGAAAATAA CACCGAAAA   1946

TAAAAATTTA AATAGTAGAC ACGTTTAATG ACTTAAAAAC TAACTTTTTC ATATCTAAT   2006

TTGTAAAATG GGCGGAAAAA GCTTAAGAAT ATGTTATTTT ACAAATCAGA GCGCTGACA   2066

ATATAGAGAG CTATATGATA TGAGTGAGAG CAACTCTCCC GTATATGCTA AGAATATTG   2126

CGCTTATTAG GATTGAAAGA TAGGATCAAT GAGGAATAAA TGTTACCCTT TTTTCTTAA   2186

AATGTAAGAG GAAATTATGA AATATACTCT GATTTGTTTA TTATTGATTA AGAACAATA   2246

AATAACCGCT CTGGTAGCTA CTGTACATAT AATTTGACGG CATATATTGC TCATATATA   2306

AACTACCGCA TTACTTCCAG TTGATAGATT TTTAACTCAG TTTCAGTACT GCCAGAACT   2366

CTCATTCGAG ATTTTTTCTA TTTTTAGAAT AGGTAAAATT GCACTTAAAT GTATAAGGG   2426
```

```
TGTACGAAGT GAGTGCCCAG ACTGTTACTA TGACAATTAA ACTAATGTCG ATGACCATT       2486

GTTTCGACAA CTCCATCTTC ATTTTCTTCA CGCGCCATAC TCGGATGAGA AAGAATCTT       2546

TCTCTAACTA TACATTTCCA AACGCAATGA TCAAGAAGAA AGCTAAATGT TACTTTGAG       2606

TCAATTACTG AGACATGTCA TGGGAATATG AGGAAGAAAC AAATCTACGT GTATTATAC       2666

CCGTAACATG TAGAGTAAAT ACCATAGTTA CCTATTTACC TGTGTCGATA AATGTTCAT       2726

AGCTCATAAG TGATGGGATA CATTGCTATT CCTCTGCAAT GGAAGCTT                   2774

(2) INFORMATION FOR SEQ ID NO:2:

(i) SEQUENCE CHARACTERISTICS:
         (A) LENGTH: 356 amino acids
         (B) TYPE: amino acid
         (D) TOPOLOGY: linear (ii) MOLECULE TYPE: protein (xi) SEQUENCE DESCRIPTION: SEQ ID NO:2:

Met Ser Gln Asn Ser Asn Pro Ala Val Val Leu Glu Lys Val Gly Asp
 1               5                   10                  15

Ile Ala Ile Glu Gln Arg Pro Ile Pro Thr Ile Lys Asp Pro His Tyr
                20                  25                  30

Val Lys Leu Ala Ile Lys Ala Thr Gly Ile Cys Gly Ser Asp Ile His
            35                  40                  45

Tyr Tyr Arg Ser Gly Gly Ile Gly Lys Tyr Ile Leu Lys Ala Pro Met
    50                  55                  60

Val Leu Gly His Glu Ser Ser Gly Gln Val Val Glu Val Gly Asp Ala
65                  70                  75                  80

Val Thr Arg Val Lys Val Gly Asp Arg Val Ala Ile Glu Pro Gly Val
                85                  90                  95

Pro Ser Arg Tyr Ser Asp Glu Thr Lys Glu Gly Arg Tyr Asn Leu Cys
            100                 105                 110

Pro His Met Ala Phe Ala Ala Thr Pro Pro Ile Asp Gly Thr Leu Val
        115                 120                 125

Lys Tyr Tyr Leu Ser Pro Glu Asp Phe Leu Val Lys Leu Pro Glu Gly
    130                 135                 140

Val Ser Tyr Glu Glu Gly Ala Cys Val Glu Pro Leu Ser Val Gly Val
145                 150                 155                 160

His Ser Asn Lys Leu Ala Gly Val Arg Phe Gly Thr Lys Val Val Val
                165                 170                 175

Phe Gly Ala Gly Pro Val Gly Leu Leu Thr Gly Ala Val Ala Arg Ala
            180                 185                 190

Phe Gly Ala Thr Asp Val Ile Phe Val Asp Val Phe Asp Asn Lys Leu
        195                 200                 205

Gln Arg Ala Lys Asp Phe Gly Ala Thr Asn Thr Phe Asn Ser Ser Gln
    210                 215                 220

Phe Ser Thr Asp Lys Ala Gln Asp Leu Ala Asp Gly Val Gln Lys Leu
225                 230                 235                 240

Leu Gly Gly Asn His Ala Asp Val Val Phe Glu Cys Ser Gly Ala Asp
                245                 250                 255

Val Cys Ile Asp Ala Ala Val Lys Thr Thr Lys Val Gly Gly Thr Met
            260                 265                 270

Val Gln Val Gly Met Gly Lys Asn Tyr Thr Asn Phe Pro Ile Ala Glu
        275                 280                 285
```

```
Val Ser Gly Lys Glu Met Lys Leu Ile Gly Cys Phe Arg Tyr Ser Phe
    290                 295                 300

Gly Asp Tyr Arg Asp Ala Val Asn Leu Val Ala Thr Gly Lys Val Asn
305                 310                 315                 320

Val Lys Pro Leu Ile Thr His Lys Phe Lys Phe Glu Asp Ala Ala Lys
                325                 330                 335

Ala Tyr Asp Tyr Asn Ile Ala His Gly Gly Glu Val Val Lys Thr Ile
            340                 345                 350

Ile Phe Gly Pro
        355
```

(2) INFORMATION FOR SEQ ID NO:3:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
CGACATATAA AAGGCTCAAT GTCTTACCGT TCATCTTTAT GAAGAGATAT AGTATAAGTG      60

GAAAAAGAA ACATCAAACA ATCAACAAGA AAAATACTA AAAAAAAAAA TTGAAAAATA      120

TTACCATGGA TCCCCGGGGT CGACTGAATA AATGAGTCGC GA                       162
```

(2) INFORMATION FOR SEQ ID NO:4:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: YES (vi) ORIGINAL SOURCE:
        (A) ORGANISM: SACCHAROMYCES CEREVISIAE (xi) SEQUENCE DESCRIPTION: SEQ ID NO:4:

```
CCCGGGTGCT AGCCAATGGG CCGGTCCGAG TCGAGGAAGA ACCGC                     45
```

(2) INFORMATION FOR SEQ ID NO:5:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
TCGCGACTCA TTTATTCAGT CGACCCCGGG GATCCATGGT AATATTTTTC AATTTTTTTT     60

TTTGATATTT TTTCTTGTTG ATTGTTTGAT GTTTCTTTTT TCCACTTATA CTATATCTCT    120

TCATAAAGAT GAACGGTAAG ACATTGAGCC TTTTATATGT                          160
```

(2) INFORMATION FOR SEQ ID NO:6:

(i) SEQUENCE CHARACTERISTICS:
        (A) LENGTH: 43 base pairs
        (B) TYPE: nucleic acid

```
            (C) STRANDEDNESS: double
            (D) TOPOLOGY: linear (ii) MOLECULE TYPE: DNA (genomic)

(iii) HYPOTHETICAL: YES (xi) SEQUENCE DESCRIPTION: SEQ ID NO:6:

GGTTCCTCGA CTCGGACCGG CCCATGGCTA GCACCCGGGA GCT                          43

(2) INFORMATION FOR SEQ ID NO:7:

(i) SEQUENCE CHARACTERISTICS:
            (A) LENGTH: 46 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: YES (xi) SEQUENCE DESCRIPTION: SEQ ID NO:7:

CATGACTCAA AATAGTAACC CTGCAGTAGT TCTAGGATCC CCCGGG                       46

(2) INFORMATION FOR SEQ ID NO:8:

(i) SEQUENCE CHARACTERISTICS:
            (A) LENGTH: 48 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: YES (xi) SEQUENCE DESCRIPTION: SEQ ID NO:8:

TCGACCCGCC GGATCCTAGA ACTACTGCAG GGTTACTATT TTGAGACA                     48

(2) INFORMATION FOR SEQ ID NO:9:

(i) SEQUENCE CHARACTERISTICS:
            (A) LENGTH: 46 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:9:

AATATTACCA TGGATCCCCG GGGTCGACTG AATAAATGAG TCGCGA                       46
```

ENHANCED YEAST EXPRESSION USING REGULATORY CONTROL SEQUENCES FROM YEAST SORBITOL DEHYDROGENASE GENE

This is a division of copending U.S. patent application Ser. No. 07/998,226, filed on Dec. 30, 1992.

FIELD OF THE INVENTION

The present invention is directed to recombinant DNA technology utilizing yeast host systems. In particular, the present invention is directed to a nucleotide sequence or fragment from a yeast sorbitol dehydrogenase gene which is capable of providing increased expression of foreign proteins in yeast.

BACKGROUND OF THE INVENTION

Developments in recombinant DNA technology have enabled cloning and expression of foreign genes in yeast. The utility of yeasts such as Saccharomyces cerevisiae as hosts for expressing mammalian and other foreign polypeptides offers advantages lacking in more commonly used prokaryotic hosts such as Escherichia coli. For example, yeasts are capable of glycosylation while prokaryotic hosts are not. The genetic system of S. cerevisiae is well-characterized, as are the principles for controlling gene expression. Additionally, S. cerevisiae is generally approved by the Food and Drug Administration.

The great practical and economic utilities of the yeast host system have been the impetus to attempt to maximize yeast expression by identifying various promoter regions to direct transcription, various sequences to terminate transcription, and other regulatory sequences. For example, yeast alcohol dehydrogenase has been identified as having a single strong promoter which is highly useful in enabling the attainment of substantial levels of expression for a variety of genes in yeast [Hitzeman, et al., Nature, 295: 717–722 (1981)]. U.S. Pat. No. 5,139,936 discloses a cloning vector containing a foreign gene and the yeast galactosidase (GAL1) regulatory region and promoter in position to increase expression of the foreign gene. U.S. Pat. No. 5,089,398 discloses the use of the promoter region from the glyceraldehyde-3-phosphate dehydrogenase to control expression of a foreign polypeptide in yeast. Thus, it is capable of providing which permits the attainment of substantial levels of expression for a variety of genes in yeast.

SUMMARY OF THE INVENTION

According to the present invention, it has been unexpectedly and surprisingly discovered that the promoter, terminator, and certain other regulatory regions from the yeast sorbitol dehydrogenase ("SDH") gene can be incorporated into expression vectors to significantly increase yields of foreign polypeptide in yeast.

In particular the present invention provides a DNA segment isolated from a Saccharomyces cerevisiae sorbitol dehydrogenase gene which is utilized to increase production of a heterologous polypeptide when the DNA segment and gene encoding the heterologous polypeptide are operably linked in a vector whereby the vector is replicated and carried by a host yeast cell. The finctionally active portion of the DNA segment is under the control of transcriptional and translation initiation and termination regulatory sequences of the sorbitol dehydrogenase gene.

The present invention further provides expression vectors capable of expression in yeast of a gene encoding a heterologous polypeptide. In particular, a vector of the present invention comprises DNA sequences under the control of transcriptional and translation initiation and termination regulatory sequences of the sorbitol dehydrogenase gene of Saccharomyces cerevisiae and a yeast replication system.

According to one embodiment of the present invention, a heterologous polypeptide is expressed in yeast by introducing a regulatory nucleotide segment from a Saccharomyces cerevisiae sorbitol dehydrogenase gene, which is induced by sorbitol, operably linked to a gene encoding a heterologous polypeptide in a vector whereby the vector is replicated and carried by the cell and the polypeptide expressed under inducing conditions.

According to another embodiment of the present invention, Saccharomyces cerevisiae is transformed with an expression vector comprising a DNA sequence under the control of transcriptional and translation initiation and termination regulatory sequences of the sorbitol dehydrogenase gene of Saccharomyces cerevisiae and a yeast replication system.

The present invention still further provides a DNA molecule comprising the nucleotide sequence of FIG. 1 [SEQ ID NO:1], or degenerate equivalents thereof, wherein the polypeptide coded for by the DNA molecule has the biological activity of yeast sorbitol dehydrogenase. A substantially purified and isolated sorbitol dehydrogenase activity from Saccharomyces cerevisiae. is also provided.

Additionally, the present invention provides an assay reagent and an improvement in various assay methods known in the art which use heterologous polypeptides as reagents, or for the preparation of reagents, such as for the production of antibodies thereto. The heterologous polypeptide is produced by yeast cells transformed with a cloning vector which has a DNA insert under the control of a transcriptional sequence, a translation initiation sequence and a termination regulatory sequence of the sorbitol dehydrogenase gene. A test kit for use in detecting the presence of a member of a specific binding pair in a test sample is also provided which test kit comprises a container containing at least one SDH-expressed heterologous polypeptide or specific binding member thereof.

BRIEF DESCRIPTION OF THE DRAWINGS

FIG. 1 [SEQ ID NO:1]illustrates the nucleotide sequence of the sorbitol dehydrogenase gene with translation of the open reading frame. Nucleic acid number 1–771 denote the transcriptional regulatory unit. Nucleic acid numbers 1846–2759 denote the transcriptional termination unit.

DETAILED DESCRIPTION OF THE INVENTION

A. DEFINITIONS

Figure 2A:
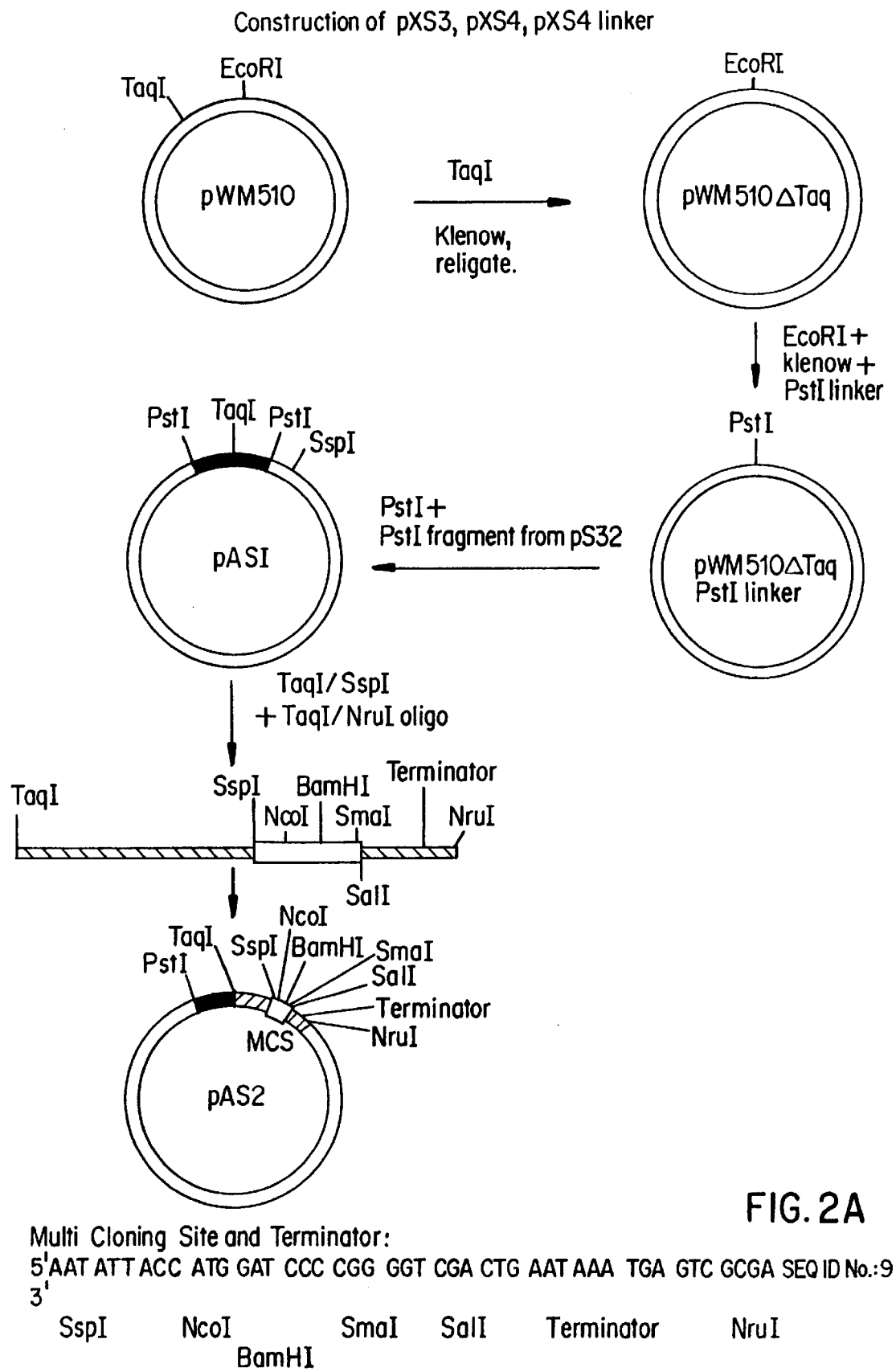
FIG. 2 is a schematic representation illustrating the construction of plasmids pxS3, pxS4, pxS4 linker. These vectors have a multiple cloning site flanked by promoter and terminator sequences of the SDH gene. Polypeptides are expressed as unfused molecules in pxS2, pxS3 and pxS4. The nucleotide sequence of the Multiple Cloning Site and Terminator of pAS2 is SEQ ID NO:9. The nucleotide sequence shown of the MCS of pXS4Linker is formed by insertion of the adaptor DNA comprising SEQ ID NO:7 and SEQ ID NO:8.

The following terms are defined as used herein:

"Biological activity" of sorbitol dehydrogenase refers to a polypeptide having preferential oxidizing specificity for sorbitol as substrate.

"DNA expression vector" is any autonomous element capable of replicating in a host independently of the host's chromosome, after additional sequences of DNA have been incorporated into the autonomous element's genome.

"Gene" is a segment of DNA, a portion of which codes for a specific polypeptide or RNA molecule.

"Heterologous polypeptide" is a protein that is not normally produced by or required for viability of a yeast organism. This term contemplates the functional insertion of DNA encoding such polypeptide, employing recombinant DNA technology, into an expression vehicle, which in turn is used to transform a yeast organism host. Functional insertion of DNA denotes the insertion of DNA encoding the heterologous polypeptide into an expression vector under control of a promoter system, as defined below. The heterologous polypeptide according to the present invention includes, but is not intended to be limited to, hormones, such as human growth hormone, bovine growth hormone, leutinizing hormone (LH), thyroid stimulating hormone (TSH), follicle stimulating hormone (FSH) and the like; lymphokines; enzymes, such as superoxide dismutase, creatinine kinase MB (CK-MB) and the like; interferons, such as human fibroblast and the like; viral antigens or immunogens, such as foot and mouth disease antigens, influenza antigenic polypeptide, hepatitis delta antigen, hepatitis B core antigen, hepatitis surface antigen, hepatitis B e antigen, human immune deficiency virus 1 and 2 (HIV 1 and 2); human T-cell leukemia virus 1 and 2 (HTLV) and the like; and various other polypeptides, such as rennin, human serum albumin, human insulin, human insulin-like growth factor-1, various glycoproteins, and the like. The heterologous polypeptide according to the present invention can be used in pharmaceutical compositions, such as vaccines and the like, to treat and/or prevent affective disorders.

"Promoter" is a DNA sequence generally described as the 5' region of a gene, located proximal to the start codon. At the promoter region, transcription or expression of an adjacent gene is initiated. This is referred to as the transcription initiation site. At the promoter region may be a sequence of nucleotides that interacts as a control over the expression of any operably linked structural gene or genes.

"Operably linked" is the control exerted by the promoter over the initiation of expression of the polypeptide encoded by a structural gene.

"Transcription initiation site" is a DNA sequence of a promoter to which RNA polymerase binds, thereby initiating transcription of succeeding codons in a 5' to 3' direction.

"Transcription terminator" is a DNA sequence at the end of the transcript that causes RNA polymerase to terminate transcription.

B. Yeast Expression Vector

According to the present invention, a particular DNA segment is linked to a gene foreign to the yeast genome and incorporated into a modified strain of S. cerevisiae so that it produces a polypeptide under the control of transcriptional and translation initiation and termination regulatory sequences of the sorbitol dehydrogenase gene of S. cerevisiae. Expression is achieved by transformation of S. cerevisiae with a novel recombinant DNA expression vector.

In particular, a yeast expression vector is provided comprising (i) a yeast selective marker, (ii) a yeast origin of replication and (iii) yeast promoter and terminator sequences of the sorbitol dehydrogenase gene of S. cerevisiae positioned relative to a unique restriction site in such a way that expression may be obtained of a polypeptide coding sequence inserted at the restriction site. In particular a non-fusion vector cassette and a fusion vector cassette containing eleven amino acids from the amino terminus of the sorbitol dehydrogenase polypeptide have been constructed. Both cassettes have been inserted into a 30 copy yeast plasmid containing the yeast TRP1 gene as a selectable marker and 2 micron origin of replication. Fusion with eleven amino acids of the sorbitol dehydrogenase polypeptide results in several fold higher levels of expression of the fused polypeptides as compared to the unfused polypeptide. In addition, expression levels of heterologous polypeptides with sorbitol dehydrogenase as a fusion partner are several fold elevated over that of sorbitol dehydrogenase itself when expressed in multi-copy plasmids. Such polypeptides provide reagents for assays which are safer and more cost effective than lysates produced from the native organisms.

Any yeast replication origin known in the art may be used to construct the vector. For example, the replication region of the natural yeast plasmid 2 micron is described by the present invention. This plasmid is cryptic in that it confers no readily detectable phenotype and is present in about 100 copies per cell.

The SDH promoter of the present invention is preferably about a 771 base pair sequence from the yeast genome which contains signals for transcription of the SDH gene into mRNA and subsequent translation of the mRNA. Although the coding sequence for sorbitol dehydrogenase is not present in this DNA fragment, the fragment can direct the expression of foreign genes and the regulation follows the mode for the SDH gene.

The SDH terminator of the present invention is preferably about a 913 nucleotide sequence which includes the poly A addition site AATAAA.

The present invention provides for the expression of fused or unfused polypeptides from yeast. There is an unique restriction site XbaI at the 5' end of the gene within the coding sequence. Insertion of DNA sequences at this site results in the production of hybrid proteins containing the N-terminal eleven amino acids of the sorbitol dehydrogenase polypeptide fused to the amino acids coded for by the inserted DNA. Genetic information contained within this sequence that may confer high level expression of sorbitol dehydrogenase results in an increased level of expression of the fusion protein.

The yeast strain of the present invention is *S. cerevisiae*, a common laboratory strain of yeast used for its low toxicity and well known genetic characteristics. This strain is readily cultivated on a large scale. The recombinant DNA material of the present invention containing a DNA segment is under the control of transcriptional and translation initiation and termination regulatory sequences of the sorbitol dehydrogenase gene and is used to express a polypeptide product in any yeast cell capable of transformation, including, but not limited to, yeast mutants that alter regulation, and the like.

The vast majority of yeasts can be cultivated under relatively uniform conditions utilizing common laboratory media and methods known in the art. As would be understood by one skilled in the art, the typical growth requirements of yeast comprise an organic carbon compound for carbon and energy, organic or inorganic nitrogen for the synthesis of polypeptides and nucleic acids, various minerals, and a mixture of vitamins. Such growth requirements are met by yeast nitrogen base (YNB), a chemically defined medium which contains a number of trace elements, vitamins, trace amounts of amino acids to stimulate growth, and the principal minerals potassium phosphate, magnesium sulfate, sodium chloride, and calcium chloride. The nitrogen source is ammonium sulfate. The desired carbon source is added at a concentration of from between about 0.5% and between about 3%. The pH range of the medium is usually from between about pH 3.0 and about pH 8.0, preferably from between about pH 4.5 and about pH 6.5.

Microorganisms prepared by the genetic engineering processes described herein are exemplified by cultures now on deposit with the American Type Culture Collection, 12301 Parklawn Drive, Rockville, Md., and are identified as follows:

Accession Number 69249, Strain *Escherichia coli*, deposited Mar. 9, 1993;

Accession Number 69250, Strain *Escherichia coli*, deposited Mar. 9, 1993;

Accession Number 69251, Strain *Escherichia coli*, deposited Mar. 9, 1993; and

Accession Number 69252, Strain *Escherichia coli*, deposited Mar. 9, 1993.

C. Assay Formats

The present invention provides an improvement to methods for detecting antigens or antibodies in a specimen from an individual, wherein a recombinant antigen employed in the method is expressed as a fused or unfused polypeptide by a vector in yeast and wherein the expression of the recombinant antigen is under the control of a DNA segment from a *Saccharomyces cerevisiae* sorbitol dehydrogenase gene which increases expression of the gene coding for the polypeptide.

An assay reagent comprising an SDH-expressed heterologous polypeptide, or specific binding member thereof is provided. Preferably, the SDH-expressed heterologous polypeptide can be an enzyme. Most perferably, the SDH-expressed heterologous polypeptide can be superoxide dismutase. The assay reagent of the present invention can be used in any diagnostic assays known in the art. The assay preferably is performed as an immunoassay, although the present invention is not limited to immunoreactive assays. Any assay utilizing specific binding members can be performed. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding member, for example, an analyte-analog. Immunoreactive specific binding members include antigens, antigen fragments; antibodies and antibody fragments, both monoclonal and polyclonal; and complexes thereof, including those formed by recombinant DNA methods.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein in the capture and/or indicator reagents for the determination of vitamin $B_{12}$, or the use of a lectin in the capture and/or indicator reagents for the determination of a carbohydrate. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances.

"Solid phases" ("solid supports") are known to those in the art and include the walls of wells of a reaction tray, test tubes, polystyrene beads, magnetic beads, nitrocellulose strips, membranes, microparticles such as latex particles, and others. The "solid phase" is not critical and can be selected by one skilled in the art. Thus, latex particles, microparticles, magnetic or non-magnetic beads, membranes, plastic tubes, walls of microtiter wells, glass or silicon chips and sheep red blood cells are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated tot he capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, and other configurations known to those of ordinary skill in the art.

The test sample can be a mammalian biological fluid such as whole blood or whole blood components including red blood cells, white blood cells including lymphocyte or lymphocyte subset preparations, platelets, serum and plasma; ascites; saliva; stools; cerebrospinal fluid; urine; sputum; trachael aspirates and other constituents of the body which may contain or be suspected of containing the analyte (s) of interest. The test sample also can be a culture fluid supernatant, or a suspension of cultured cells. Mammals whose body fluids can be assayed for antigen analyte or antibody analyte according to the present invention include humans and primates, as well as other mammals who are suspected of containing these analytes of interest. It also is contemplated that non-biological fluid samples can be utilized.

The assay reagent of the present invention includes an indicator reagent comprising a label conjugated to a specific binding member of each analyte. Each indicator reagent produces a detectable signal at a level relative to the amount of the analyte in the test sample. In a preferred embodiment, each indicator reagent, while comprising a specific binding member of a different analyte, is conjugated to the same signal generating compound (label), which is capable of generating a detectable signal. In general, the indicator reagent is detected or measured after it is captured on the solid phase material. In the present invention, the SDH-expressed polypeptide includes one or more components of the indicator reagent(s). It is contemplated that different signal generating compounds can be utilized in the practice of the present invention. Thus, for example, different fluorescent compounds could be utilized as the signal generating compounds, one for each indicator reagent, and detection could be determined by reading at different wavelengths. Or, a short-lived chemilulminescent compound such as an acridinium or phenanthrindium compound and a long-lived chemiluminescent compound such as a dioxetane can be utilized to generate signals at different times for different analytes. Methods which detail the use of two or more chemiluminescent compounds which are capable of generating signals at different times are the subject matter of co-pending patent application U.S. Ser. No. 636,038, which enjoys common ownership and is incorporated herein by reference. Acridinium and phenanthridinium compounds are described in co-pending U.S. patent application Ser. No. 07/271,763 filed Jun. 23, 1989, which enjoys common ownership and is incorporated herein by reference.

In addition to being either an antigen or an antibody member of a specific binding pair, the specific binding member of the indicator reagent can be a member of any specific binding pair, including either biotin or avidin, a carbohydrate or a lectin, a complementary nucleotide sequence, an effector or a receptor molecule, an enzyme cofactor or an enzyme, an enzyme inhibitor or an enzyme, and the like. An immunoreactive specific binding member can be an antibody, an antigen, or an antibody/antigen complex that is capable of binding either to the analyte as in a sandwich assay, to the capture reagent as in a competitive assay, or to the ancillary specific binding member as in an indirect assay. If an antibody is used, it can be a monoclonal antibody, a polyclonal antibody, an antibody fragment, a recombinant antibody, a mixture thereof, or a mixture of an antibody and other specific binding members. The details of the preparation of such antibodies and their suitability for use as specific binding members are well known to those in the art.

The heterologous polypeptide produced by the present invention can be the signal generating compound (label) of the indicator reagent which is capable of generating a measurable signal detectable by external means. The various signal generating compounds labels) contemplated include chromagens; catalysts such as enzymes for example, superoxide dismutase, horseradish peroxidase, alkaline phospatase, and β-galactosidase. The selection of a particular label is not critical, but it will be capable of producing a signal either by itself or in conjunction with one or more additional substances. A variety of different indicator reagents can be formed by varying either the label or the specific binding member. In particular, the determination of various other immunoassay formats can be followed according to the present invention. Such immunoassay system formats include, but are not intended to be limited to, competitive, sandwich and immunometric techniques. Generally, such immunoassay systems depend upon the ability of an immunoglobulin, i.e., a whole antibody or fragment thereof, to bind to a specific analyte from a test sample wherein a labeled reagent comprising an antibody of the present invention, or fragment thereof, attached to a label or detectable moiety is employed to determine the extent of binding. Such detectable labels include, but are not intended to be limited to, enzymes, radiolabels, biotin, toxins, drugs, haptens, DNA, RNA, liposomes, chromophores, chemiluminescers, colored particles and colored microparticles, fluorescent compounds such as aminomethylfluorescein, 5-fluoresceinyl, 6-fluoresceinyl, 5-carboxyfluorescein, 6-carboxyfluorescein, aminofluorescein, thioureafluorescein, and methoxytriazinolyl-aminofluorescein, and the like fluorescent derivatives. As described herein, the test sample can be a naturally occurring or artificially formed liquid, or an extract thereof, and includes, but is not intended to be limited to biological test samples such as whole blood, serum, plasma, urine, feces, saliva, cerebrospinal fluid, brain tissue, and the like. In addition, the test sample can be an extract of a test sample, or any derivative thereof.

The use of scanning probe microscopy (SPM) for immunoassays also is a technology to which the SDH-expressed heterologous polypeptide, or specific binding member thereof, produced by the present invention are easily adaptable. In scanning probe microscopy, in particular in atomic force microscopy, the capture phase, for example, at least one of the SDH-expressed heterologous polypeptides, or specific binding members there of the invention, is adhered to a solid phase and a scanning probe microscope is utilized to detect specific binding member complexes which may be present on the surface of the solid phase. The use of scanning tunnelling microscopy eliminates the need for labels which normally must be utilized in many immunoassay systems to detect antigen/antibody complexes. Such a system is described in pending U.S. patent application Ser. No. 662,147, which enjoys common ownership and is incorporated herein by reference.

The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane. (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis (succinimidyl) suberate, SPPD 9 succinimidyl 3-[2-pyridyldithio]propionate), SMCC (succinimidyl-4-[N-maleimidomethyl]cyclohexane-1-carboxylate), SIAB (succinimidyl [4-iodoacetyl] aminobenzoate), and SMPB (succinimidyl 4-[1-maleimidophenyl]butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons (available from Sigma Chemical Co., St. Louis, Mo.). Also, polyelectrolyte interactions may be used to immobilize a specific binding partner on a surface of a test piece by using techniques and chemistries described by pending U.S. patent applications Ser. No. 150,278, filed Jan. 29, 1988, and Ser. No. 375,029, filed Jul. 7, 1989, each of which enjoys common ownership and each of which is incorporated herein by reference. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

D. Purification Methods

The assay reagent produced by the present invention can be used for isolation and purification of a member of a specific binding pair, such as an antibody, by immobilizing the assay reagent to a solid support material, such as in a column format, and contacting the assay reagent with a test sample. The member of a specific binding pair can be recovered from the immobilized assay reagent by conditions which disrupt the binding interaction between the assay reagent and the member of a specific binding pair For example, such binding interaction can be disrupted by raising or lowering the pH or by the use of protein denaturants such as urea, guanidinium, hydrochloric acid, sodium dodecyl sulfate, and the like.

C. Test Kits

The present invention additionally provides a test kit for use in detecting the presence of a member of a specific binding pair in a test sample which test kit comprises a container containing at least one SDH-expressed heterologous polypeptide produced according to the present invention. The heterologous polypeptide can be produced as a fused or unfused protein. The expression vectors described according to the present invention are capable of expressing SDH heterologous polypeptide fusions at high levels. Example 7 illustrates the expression of superoxide dismutase as an SDH fusion polypeptide.

The test kit is presented in a commercially packaged form as a combination of one or more containers holding the necessary reagents, as a composition or admixture where the compatibility of the reagents will allow. It is to be understood that the test kit can, of course, include other materials as are known in the art and which may be desirable from a commercial user standpoint, such as buffers, diluents, standards, and the like.

The present invention will now be illustrated, but is not intended to be limited by, the following examples.

EXAMPLES

General Methods

Standard methods were employed for restriction endonuclease digestion, DNA ligation and other DNA manipulation techniques such as preparation of plasmid DNA, labeling DNA by nick translation and transformation of *E. coli* as described by Maniatis et. al., Molecular Cloning, A Laboratory Manual, Cold Spring Harbor, N.Y. (1982). Transformation of yeast was done according to Percival et al. *Anal. Biochem.* 163: 391 (1987). General methods used in the manipulation of yeast are described by Sherman et al, *Methods in Yeast Genetics: A Laboratory Manual*, Cold Spring Harbor, N.Y. (1983). T4 DNA ligase, calf intestinal alkaline phosphatase and restriction enzymes were used according to the supplier's instruction (BRL).

Reagents and Enzymes

Media for growth of bacteria and yeast were purchased from Difco, Detroit, Mich. Bethesda Research Laboratories (BRL), Gaithersburg Md.; New England Biolabs, Beverley, Mass.; or Boehringer Mannheim, Indianapolis, Ind. were the vendors for restriction enzymes, calf intestinal alkaline phosphatase (CIAP) and T4 DNA ligase. Zymolyase 60T was purchased from Miles Laboratory, Elkhart, Ind. Nick Translation kit and other reagents for Nick translations were obtained from Amersham Corporation, Arlington Heights, Ill. Reagents for detecting expression in λgt11 yeast genomic library were purchased from Bio Rad, Richmond, Calif. Phenylmethyl sulfonylfluoride (PMSF) was purchased from BRL.

Host Cell Cultures, DNA Sources, Vectors,

*E. coli* K12 strain TB1 is a derivative of JM83 (BRL). Yeast strain 8000-8B (Accession Number 74215, Strain *Saccharomyces cerevisiae*, deposited Mar. 9, 1993) was provided by Dr. E. T. Young, University of Washington, Seattle, Wash. *S. cerevisiae* 8000-8B LAG- (Accession Number 74214, Strain *Saccharomyces cerevisiae*, deposited Mar. 9, 1993) was isolated as a spontaneous mutant by selecting for growth on YNB minimal plates containing 2% sorbitol as carbon source. This mutant does not exhibit the unusual lag period for growth on sorbitol medium. Further characterization of the mutant determined that it was an a/a diploid.

*E. coli* vector pUC18 was purchased from Bethesda Research Laboratories. The λgt11 yeast genomic library was obtained from Dr. M. Snyder (Stanford University, Berkeley, Calif.). Yeast vectors pMW5 (Accession Number 69249, Strain *Escherichia coli*, deposited Mar. 9, 1993) and pyCDE1 also referred to as pMAC561 were obtained from Dr. Benjamin D. Hall (University of Washington, Washington Research Foundation, Seattle, Wash.). Plasmid pWM510 (Accession Number 69251, Strain *Escherichia coli*, deposited Mar. 9, 1993) was obtained from Dr. Wlodek Mandecki (Abbott Laboratories, Abbott Park, Ill.).

All organisms described herein by an accession number have been deposited at the American Type Culture Collection (A.T.C.C.), 12301 Parklawn Drive, Rockville, Md. 20852, as of Mar. 10, 1997, under the terms of the Budapest Treaty and will be maintained for a period of thirty (30) years from the date of deposit, or for five (5) years after the last request for the deposit, or for the enforceable period of the U.S. patent, whichever is longer.

Example 1
Isolation of Sorbitol Dehydrogenase Activity in S. cerevisiae 8000-8B.

S. cerevisiae strain 8000-8B (obtained from Dr. E. T. Young, University of Washington) was grown to saturation at 30° C. in 1% yeast extract and 2% peptone ("YEP") medium containing either 2% sorbitol or mannitol as sole carbon source. Cells were pelleted by centrifugation, washed with 1 ml water and resuspended in 500 ml of buffer containing 50 mM potassium phosphate, pH 7.4, 1 mM PMSF, and 25 mM β-mercaptoethanol, hereinafter "extraction buffer". Cells were disrupted by vortexing the suspension with acid washed glass beads until cells appeared broken under the microscope. The cell extracts were then assayed for sorbitol dehydrogenase activity as described by Williamson et. al. *Nature*, 283: 214–216 (1980) and stained for enzyme activity as described in Fowler et. al. *Biochem.*, 50: 635–645 (1972), except that 0.2 ml 20% sorbitol was substituted for ethanol. Only extracts of S. cerevisiae 8000-8B grown in medium with sorbitol produced blue stained sorbitol dehydrogenase activity bands when electrophoresed on non-denaturing gel. No stained bands were visible on the same gel containing extracts from mannitol grown culture. In order to determine the approximate molecular weight of sorbitol dehydrogenase, polypeptides contained in the activity stained band were extracted from the non-denaturing gel and re-electrophoresed on an SDS-PAGE gel. A unique band of apparent molecular weight of 40,000 daltons was present only in the sorbitol-induced cells.

Example 2
Generation of Antibody to Sorbitol Dehydrogenase
Step 1: Preparation of Antigen for Antibody Production.

S. cerevisiae strain 8000-8B was grown at 30° C. to saturation in 250 ml. YEP medium containing 2% sorbitol. Large scale extracts were made by resuspending the cell pellet in 40 mL extraction buffer (described in Example 1, above) using the Bead-Beater (Biospec Products) to disrupt the cells according to the manufacturer's recommendations. Extracts were mixed with buffer containing 0.0625 M Tris pH 6.8, 2% SDS, 10% glycerol, 5% b-mercaptoethanol, hereinafter "sample buffer", boiled 3 minutes, and loaded at a quantity of 40 ml/lane into a 7.5% SDS-PAGE gel. The gel was stained for 5 minutes in 25% isopropanol, 10% acetic acid, 0.05% Coomassie blue and destained for 20 minutes in 5% methanol and 7% acetic acid. A portion of the gel containing protein(s) of approximately 40,000 daltons molecular weight was used to immunize rabbits. Antisera was prepared according to the method described by White et al. *Cell*, 39: 163–171 (1984). Rabbits were immunized with approximately 50 μg protein followed by a booster dose of 50 μg per rabbit. Subsequent booster doses of 50 μg were given at 14 day intervals following the previous booster dose.
Step 2: Isolation and Characterization of the Antibody.

Western blot analysis was used to monitor the immune response of the rabbits. S. cerevisiae strain 8000-8B was grown in YEP medium containing either 2% glucose, mannitol or sorbitol. Cell extracts were prepared as described in Example 1 and electrophoresed on 7.5% SDS-PAGE gels and on non-denaturing gels. Gels were electroblotted onto nitrocellulose, blocked with 5% Carnation nonfat dry milk in "TBS" (150 mM NaCl, 50 mM Tris pH 8.1) and incubated with 1:100,000 dilution of the rabbit antisera obtained after the first booster dose. Filters were washed twice in TBS containing 0.05% Tween 20, and twice with TBS. Filters were then incubated with BioRad goat-anti-rabbit HRP conjugated second antibody, washed and stained (BioRad Express-Blot kit) according to manufacturer's recommendations. An immunoreactive band at approximately 40,000 daltons molecular weight appeared only in the lane with the extract of sorbitol grown cells as determined by BRL pre-stained high molecular weight protein markers. An immunoreactive band was visualized on the native gel corresponding to the position of sorbitol dehydrogenase activity.

Example 3
Isolation of S. cerevisiae Sorbitol Dehydrodtenase Gene
Step 1: Isolation of Clones lS30 and lS32 Containing the S. cerevisiae Sorbitol Dehydrogenase Gene.

The yeast sorbitol dehydrogenase gene was isolated from a lgt11 yeast genomic library obtained from Dr. M. Snyder (Stanford University). Clones lS30 and lS32 were isolated using the antibody probe approach described in Synder et al. *Meth. Enzym.*, 154: 1070128(1984). E. coli strain Y1090 (obtained from Dr. M. Snyder) was grown at 37° C. over night in Luria Broth containing 50 mgm/mL ampicillin and 0.2% maltose. Cells were collected by centriflgation and the pellet resuspended in 0.4 volumes 10 mM MgSO4. An aliquot of the lgt11 library containing $10^5$ phage particles w as then mixed with 200 mL of prepared Y1090 cells. The mixture was incubated at 37° C. for 20–30 minutes to allow phage absorption. LB top agarose (6.5 mL) was added to each sample and plated onto an LB plate containing 50 mgm/mL ampicillin. The plates were incubated at 42° C. until phage plaques were barely visible (approximately 3–4 hours). The plates were overlaid with nitrocellulose discs presoaked in 10 mM isopropyl thiogalactoside (BRL) and incubated at 37° overnight. The filters were then carefully lifted off the plates and floated in a petri dish containing a solution of 0.0625 M Tris pH 6.8, 2% SDS, 10% glycerol and 5% B-ME. After incubation for 2 minutes, the filters were washed 3 times in TBS. The filters were then incubated with blocking solution (5% Carnation non-fat dry milk in TBS) at room temperature for one hour. Blocking solution was discarded and the filters were then reacted overnight at 4° C. with a solution of the rabbit antiserum diluted 1:100 in blocking solution. The filters were subsequently washed and incubated with alkaline phosphatase conjugated goat-anti-rabbit antibody as described in the BioRad Express Blot Kit. Washing and staining were performed according to manufacturer's recommendations. Positive plaques were visualized as blue plaques and a total of eight positive plaques were obtained from $6 \times 10^5$ total phage that were screened. After 4 rounds of plaque purification (as described in Maniatis et. al *Molecular Cloning: A Laboratory Manual*. Cold Spring Harbor, N.Y. (1982)), Five lambda clones λS30, λS31, λS32, λS35, and λS36 were further characterized.
Step 2: Construction of pS30 and pS32

The inserts from the five lambda clones, isolated as described above, were subcloned into the plasmid vector pUC18. Phage DNA from clones λS30, λS31, λS32, λS35, and λS36 was prepared according to the method described by Helms et. al. *DNA* 4 (1): 39–49 (1985). The DNA was digested with EcoRI, ligated to EcoRI digested pUC18 (BRL) and transformed into E. coli strain TB1. Aliquots of the transformation mixture were plated onto LB plates containing ampicillin and X-Gal (BRL) using standard methods described in Maniatis. Plasmid DNA was isolated from several white colonies and analyzed by EcoRI digestion. The EcoRI inserts in some of the lambda clones had internal EcoRI restriction sites because the λgt11 yeast genomic library was constructed from sheared yeast genomic DNA. The subcloning of EcoRI inserts from the five lambda clones therefore gave rise to eight pUC18 subclones. The sizes of the EcoRI fragments ranged from 0.5 to 4.5 kilobases.

To demonstrate the relatedness of these subelones, the 4.5 kb EcoRI insert of pS30 was used to probe the eight subclones via Southern hybridization. Both pS30 and pS32 hybridized to the pS30 insert suggesting that the two clones were related to each other. Clones pS30 and pS32 were chosen for subsequent analysis and are considered interchangeable. The EcoRI inserts in pS30 and pS32 are 4.5 Kb and 3.0 Kb respectively.

Step 3: Identification of the Sorbitol Dehydrogenase Gene Encoded in RS30

Strain 8000-8B was grown to log phase in YEP medium containing either 2% glucose, sorbitol or mannitol as a carbon source. Total RNA was prepared from the cell pellets according to the method described by Denis et. al., *Mol. Cell. Biol.*, 6(11): 4026–4030 (1986). Cell pellets were disrupted with glass beads in RNA extraction buffer (0.1M NaCl, 0.1M Tris pH 7.5, 1 mM EDTA, 0.1% SDS). RNA was precipitated from the aqueous suspension following extraction of polypeptides with a mixture of phenol, chloroform and isoamyl alcohol. Ten micrograms of total RNA from the three different cultures were electrophoresed on 1.5% agarose formaldehyde gels as described in Maniatis et. al. RNA was blotted onto Hybond-N paper, prehybridized, hybridized and washed as described in the Amersham Hybond instruction manual. Radioactive probe was made using plasmids pS30, and pPYK by nick translation using the Amersham Nick Translation Kit. Plasmid pPYK obtained from D. Olson (University of Washington, Seattle) contains coding sequences for the yeast glycolytic protein pyruvate kinase which is expressed constituitively at a high basal level. Plasmid pPYK should therefore hybridize to a specific MRNA transcript (~1.7 kb) made in the cultures grown with different sugars. The integrity of the RNA preparation was inferred from the results of Northern Blot hybridization experiments in which pPYK probe hybridized to specific ~1.7 lilobase message expressed in all three cultures. RNA ladder (BRL) was used to determine the size of the mRNA transcripts.

Step 4: Sequence Determination of the Sorbitol Dehydrogenase Gene from Yeast

Clones pS30 and pS32 were used to generate the complete DNA sequence of the sorbitol dehydrogenase gene. Sequence data was initially obtained by 5' end labeling specific fragments of overlapping genomic clones (pS30 and pS32) and subjecting them to Maxam & Gilbert chemical degradation. This data led to a more informative restriction map enabling the cloning of the three HindIII fragments from genomic clone pS32. The approximately 0.5, 0.7 and 1.5 Kb fragments were subcloned into mp11 (M13 cloning/ sequence vector). Complete sequence data was obtained for each subcloned fragment utilizing dideoxy chain terminating chemistry. Custom DNA primers for "gene walking" were employed to sequence entirely across reverse orientations of the subcloned fragments. DNA sequencing reaction products were electrophoresed on 8M urea 6% and 4% polyacrylamide gels and imaged using standard autoradiography film. The sequence of the gene is presented in FIG. 1. Analysis of the DNA sequence reveals an open reading frame that codes for a 357 amino acid polypeptide. A comparison of the deduced amino acid sequence of the yeast enzyme with the known sequence of the sheep liver enzyme revealed an 60.84% overall amino acid homology between the two polypeptides. In addition there was a strict conservation of 19 out of 22 residues of sheep liver SDH with the deduced amino acid sequence of the yeast sorbitol dehydrogenase polypeptide.

Example 4

Construction of Yeast Expression Vectors pxS2, pxS3, px4 and pxS4 Linker.

The assembly of promoter/terminator and regulatory sequences of the SDH gene in yeast plasmid pMW5 (obtained from Dr. B. D. Hall, University of Washington, Seattle, Wash.) is described below.

Plasmid pWM510 was first digested with TaqI followed by treatment with Klenow polymerase to generate DNA with blunt ends. The religated plasmid was transformed into *E. coli* TB1, clones were analyzed for the presence of pWM510 with the inactivated TaqI site. DNA from the transformant containing the construction (pWM510ΔTaq) was then treated with EcoRI, followed by Klenow polymerase; PstI linkers (BRL) were ligated to the blunt ended DNA in order to provide a unique PstI site on the plasmid.

The 0.5 kb PstI fragment containing part of the 5' promoter and coding sequences of the SDH gene was excised from pS32, prepared in Example 3, above and ligated to pWM510ΔTaqI Pst linker at the PstI site to form plasmid pAS1.

A separate analysis with TaqI/SspI identified clones with the PstI fragment in the correct orientation. pAS1 was digested with TaqI and SspI in order to replace the 143 bp. TaqllPstI fragment with synthetic adapter DNA. The unique SspI site was present on pWM510 DNA sequences downstream of the PstI site. The adapter DNA was assembled from four separate oligonucleotides which were synthesized by the Applied Biosystem 380 A synthesizer using 5' dimethoxytrityl nucleoside β-cyanoethyl phosphoramidites. The four oligonucleotides were annealed and ligated to pASI at the TaqIISspI sites. The sequence of the adapter DNA (SEQ ID NO:3 and SEQ ID NO:5, top and bottom strands, respectively) is presented below.

```
 1  5'CGACATATAAAAGGCTCAATGTCTTACCGTTCATCTTTATGAAGAGATATAGT
    3'TGTATATTTTCCGAGTTACAGAATGGCAAGTAGAAATACTTCTCTATATCA 54  5'ATAAGTGGAAAAAAGAAACATCAAACAATCAACAAGAAAAAATACTAAAAAA
    3'TATTCACCTTTTTTCTTTGTAGTTTGTTAGTTGTTCTTTTTTATGATTTTTT
```

```
                                    -continued
106 5'AAAAATTGAAAAATATTACCATGGATCCCCGGGGTCGACTGAATAAATGAGTC

3'TTTTTAACTTTTTATAATGGTACCTAGGGGCCCCAGCTGACTTATTTACTCAGCGCT 159 5'GCGA3'
```

A unique.NruI site was included at the 3' end of the adapter DNA in addition to unique cloning sites NcoI, BamHI, SmaI and SalI. Transformants containing the ligated DNA were analyzed for the presence of the adapter molecule by analysis of mini-prep DNA with NruI and PstI. Plasmid pAS2, was identified as having the adapter DNA.

In a separate experiment the 3 kb EcoRI yeast DNA fragment containing the SDH gene was excised from pS32 and ligated into pWM510 ΔTaq at the EcoRI site. The PstI/NruI fragment containing the adapter DNA with unique cloning sites was obtained from pAS2, and inserted into pWM510ΔTaq S32 at the PstI and NcoI sites. This manipulation was done after the NcoI site was treated with Klenow polymerase. The transformant containing plasmid pAS3, with the adapter DNA was identified from EcoRI restriction analysis of mini prep DNA which released 1.5, 2, kb fragments. The EcoRI fragment containing the SDH expression cassette with promoter, terminator, and regulatory sequences from the SDH gene was then transferred into the yeast plasmid pMW5 at the EcoRI site. pMW5 was previously engineered to remove the unique BamHI site. The transformant containing the SDH cassette was identified by EcoRI restriction analysis of DNA from several isolates. Plasmids pXS2 and pXS3 had the correct 2 kb insert. Plasmid pXS2 was further shown to contain two SDH expression cassettes as determined by digestion with XhoI. In order to construct a yeast expression plasmid with an unique SalI site, the EcoRI fragment for pXS3 was excised and ligated to the yeast plasmid pMW5ΔBamΔSal (pMW5 re-engineered to inactivate the BamHI and SalI sites). Clones containing the plasmid pxS4 with unique NcoI, BamHI, SmaI, SalI sites were identified by restriction analysis of plasmid DNA prepared from several transformants.

Figure 2B:
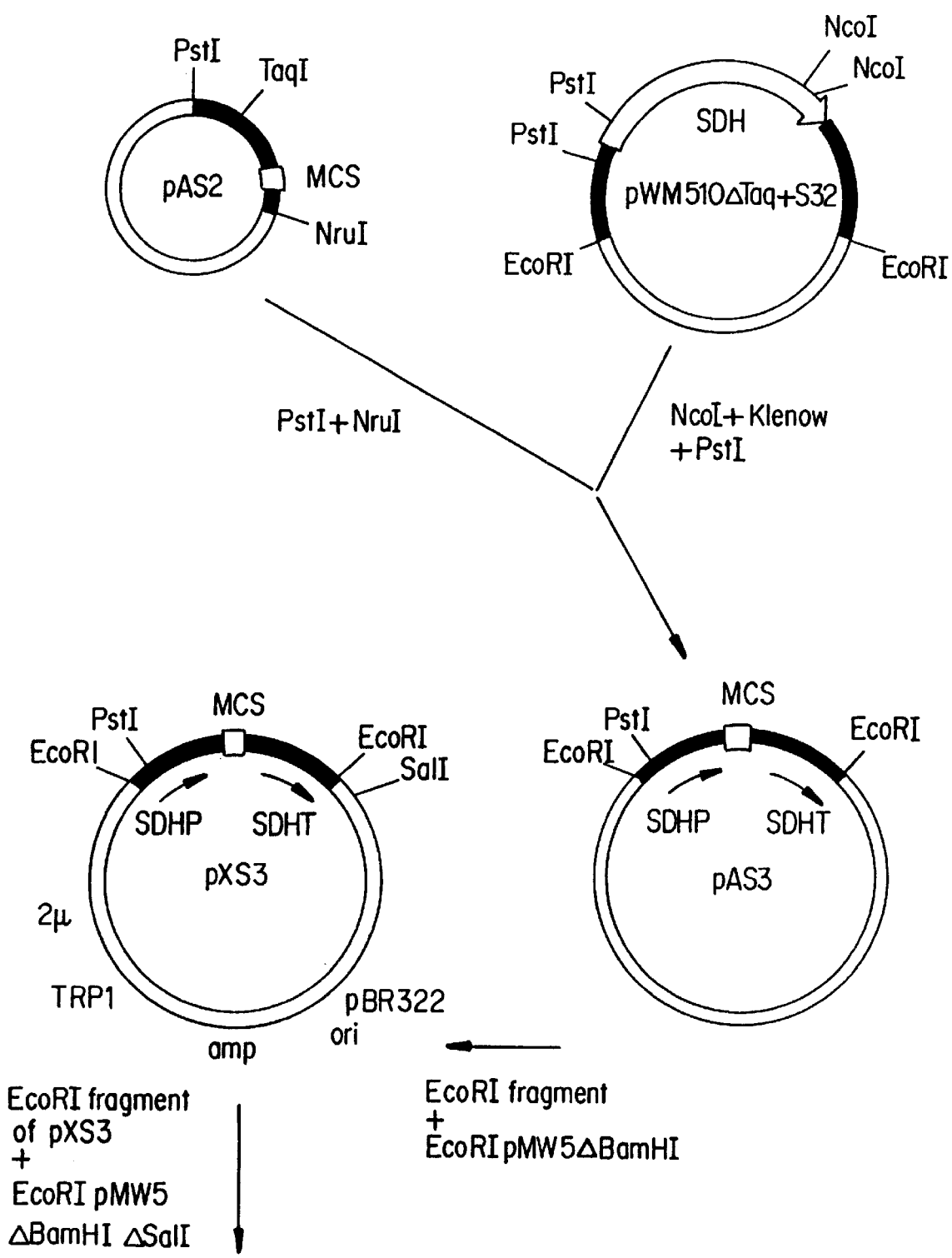
Figure 2C:
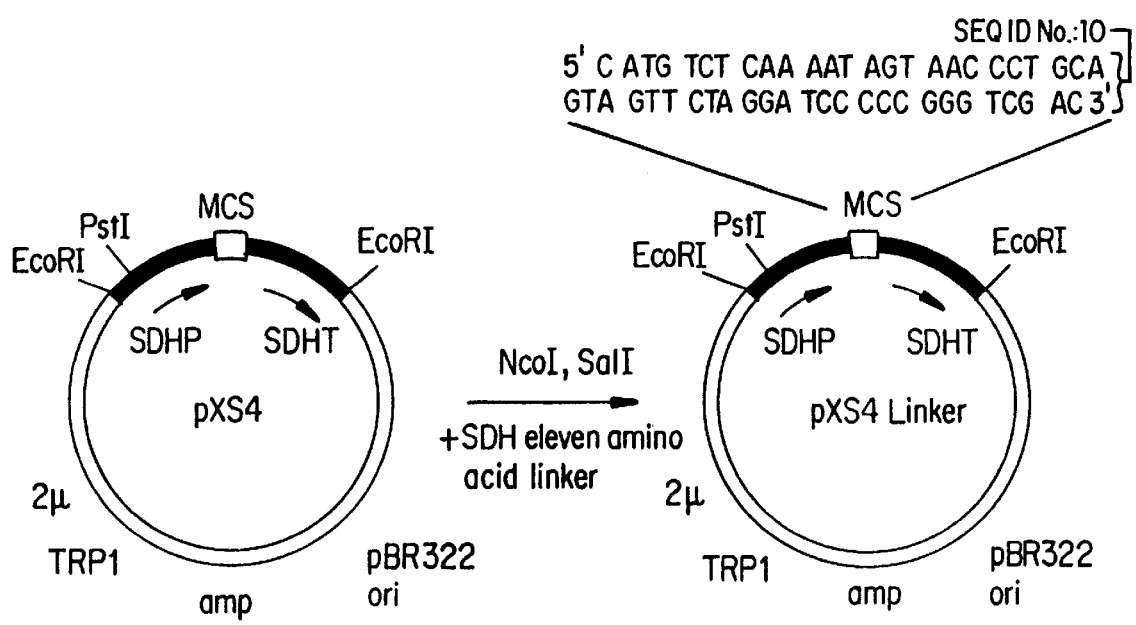

The construction of pxS4 linker which contains the SDH expression cassette containing promoter/terminator and coding sequences for N-terminal amino acids of the sorbitol dehydrogenase polypeptide is presented in FIG. 2. Two oligonucleotides were synthesized by the Applied BioSystems 340A synthesizer as described previously. The two oligonucleotides when annealed and ligated into the NcoI/SalI sites of pxS4 should result in an SDH expression cassette containing coding sequences for the N-terminal eleven amino acids of the sorbitol dehydrogenase polypeptide. The NcoI site at the initiator ATG codon was also destroyed in this construction. The adapter DNA provides unique BamHI, SmaI and SalI cloning sites. The sequence of the adapter DNA is presented below.

```
5'CATGTCTCAAAATAGTAACCCTGCAGTAGTTCTAGGATCCCCCGGG3'        (SEQ ID NO:7)

3'  AGAGAGTTTTATCATTGGGACGTCATCAAGATCCTAGGGGGCCCAG CT5'(SEQ ID NO:8)
```

Plasmid DNA pxS4 was digested with NcoI and SalI, ligated with several fold excess of the annealed oligonucleotides and transformed into E. coli TB1. Transformants were isolated on LB plates containing ampicillin at a concentration of 50 mgm/liter. DNA from several transformants was purified and restricted with NcoI. Plasmid DNA was extracted from the isolate containing plasmid without the NcoI site. Individual digests with NcoI, BamHI, SmaI, SalI and EcoRI confirmed that the isolate contained the adapter DNA. This plasmid was named pxS4 linker.

Example 5

Expression of Hepatitis Delta Antigen in Yeast using Expression Vector pxS3.

Step 1: Construction of pxS3 Delta.

Figure 3A:
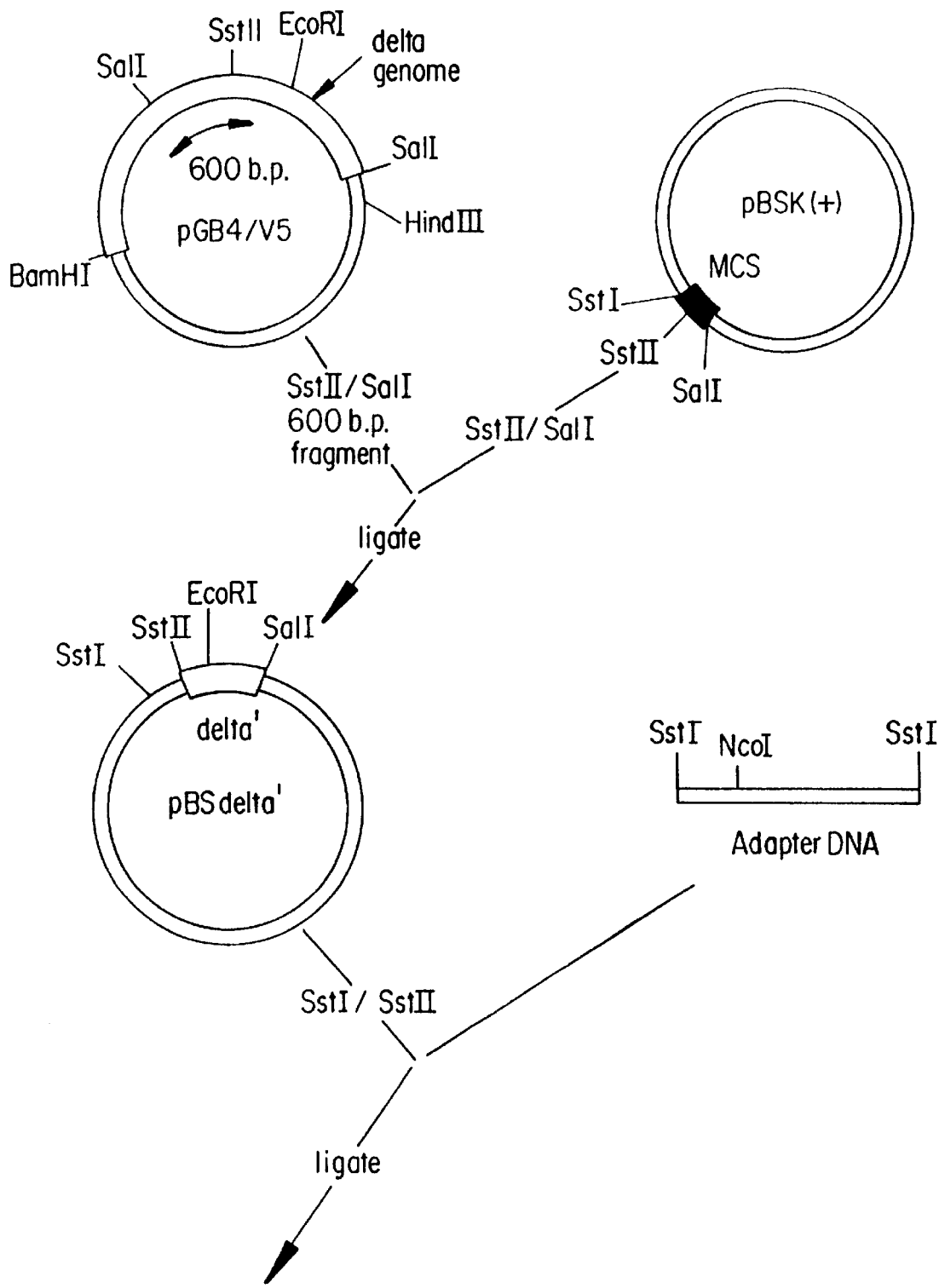
FIG. 3 is a schematic representation illustrate the construction of pxS3 containing the gene for hepatitis delta antigen.
Figure 3B:
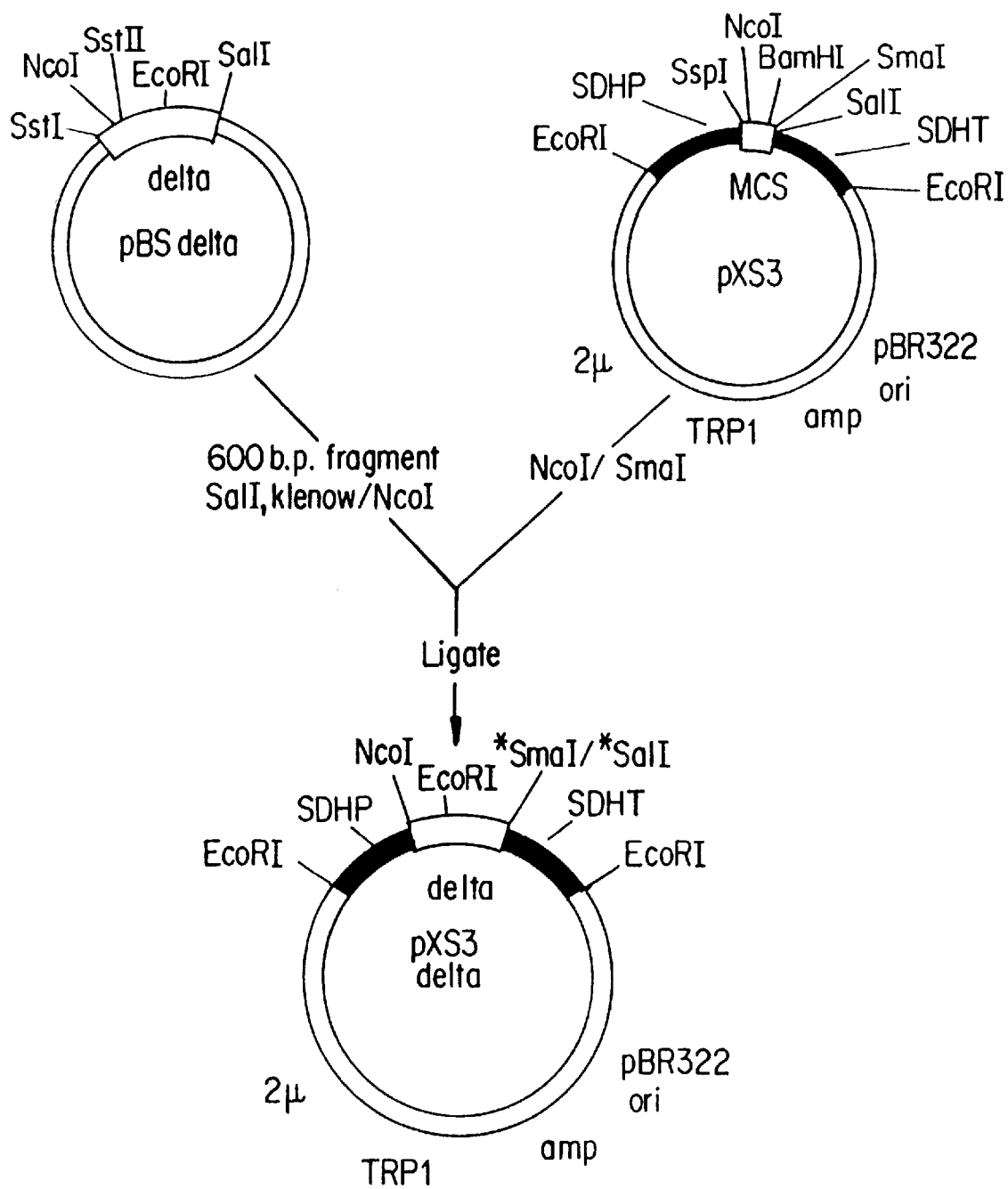

DNA coding for the hepatitis delta antigen was obtained from pGB4-V5 (obtained from Dr. J. Taylor, Fox Chase Cancer Center, Philadelphia, Pa.). A 600 base pair SstII/SalI fragment containing most of the delta antigen sequence was first subcloned into pBSK+(Stratagene) at the SstII/SalI sites (FIG. 3). Transformants containing the 600 base pair fragment were identified by restriction analysis of plasmid DNA with SstII and SalI. Clone pBSdelta' was identified as having the correct insert.

Synthetic adapter DNA coding for the N-terminal nine amino acid residues that are absent from the SstII/SalI fragment of the delta antigen gene was ligated to pBSdelta' at the SstI/SstII sites. The sequence of the adapter DNA (SEQ ID NO:4 and SEQ ID NO:6, top and bottom strands, respectively) is presented below.

```
5'CCCGGGTGCTAGCCATGGGCCGGTCCGAGTCGAGGAAGAACCGC3'

3'TCGAGGGCCCACGATCGGTACCCGGCCAGGCTCAGCTCCTTGG5'
```

The clone containing plasmid pBS delta was identified by restriction analyses with NcoI; the NcoI/SalI fragment was then inserted into the NcoI/SmaI sites of pxS3. The SalI end of the fragment was first blunt ended with Klenow polymerase. Restriction analysis of plasmid DNA with EcoRI identified clones containing DNA coding for the entire delta antigen polypeptide. The diagnostic EcoRI site in the delta antigen gene was used to confirm the identity of pxS3 delta.

Step 2: Western Blot Analysis of S. cerevisiae 8000-8B LAG Expressing the Hepatitis Delta Antigen from pxS3 Delta.

S. cerevisiae 8000-8B LAG as described above was made competent as described by Percival et al. Anal. Biochem. 163: 391 (1987), and transformed with pxS3 delta, and the transformants were isolated and repurified on YNB minimal—TRP plates. Individual transformants were grown in YNB minimal medium under selection; 2% sorbitol was added to provide both a carbon source and inducer for the SDH promoter. Cells were grown at 30° C. for 48 hours. Cell pellets were washed in distilled water and resuspended in lysis buffer (0.05M $KPO_4$, pH 7.4, 1 mM PMSF). Cell lysates were prepared by disrupting the cells with glass beads for 90 seconds. Expression of the hepatitis delta antigen was determined by Western Blot Analysis.

Figure 4:
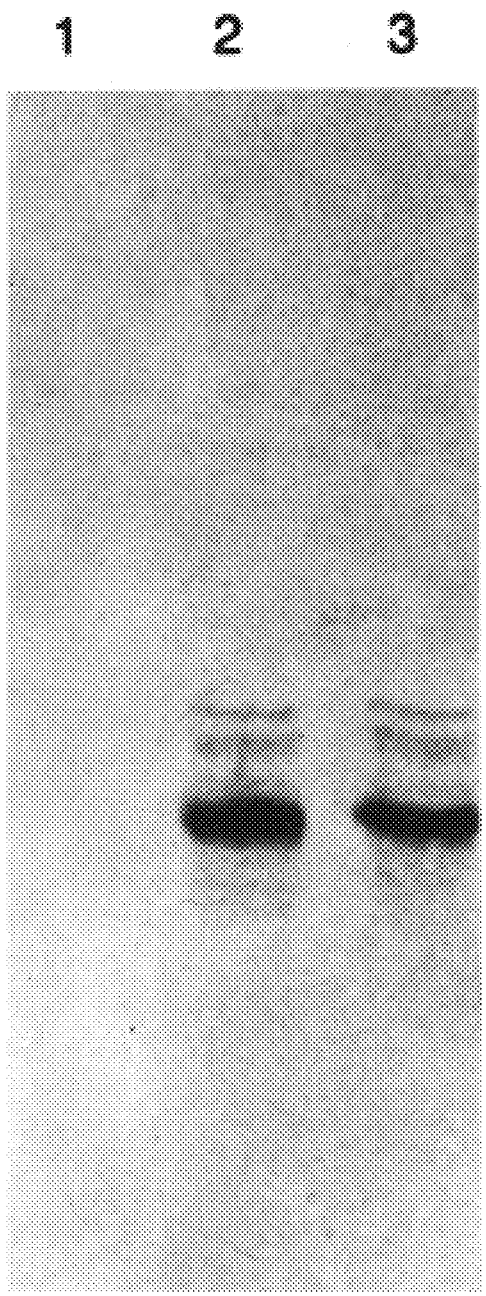
FIG. 4 illustrates the Western Blot analysis of hepatitis delta antigen expression in transformants containing pxS3 delta. Cell extract from transformants containing pxS3, was electrophoresed in lane 1 on SDS PAGE. Lysates from 2 individual transformants containing pxS3 delta were loaded in lanes 2,3. Analysis was done by Western Blot analysis using human serum containing antibody to the delta antigen.

Detection of hepatitis delta antigen expression by Western Blot analysis of extracts electrophoresed on SDS-PAGE is presented in FIG. 4. A strong immunoreactive band is evidenced only in lanes 2, and 3 which contain extracts of transformants expressing the hepatitis delta antigen. This data conclusively demonstrates the production of hepatitis delta antigen from plasmid pxS3.

Example 6
Use of pxS2 to Express the Human Superoxide Dismutase Polypeptide in 8000-8B LAG.
Step 1: Construction of pxS2-SOD.

Figure 5A:
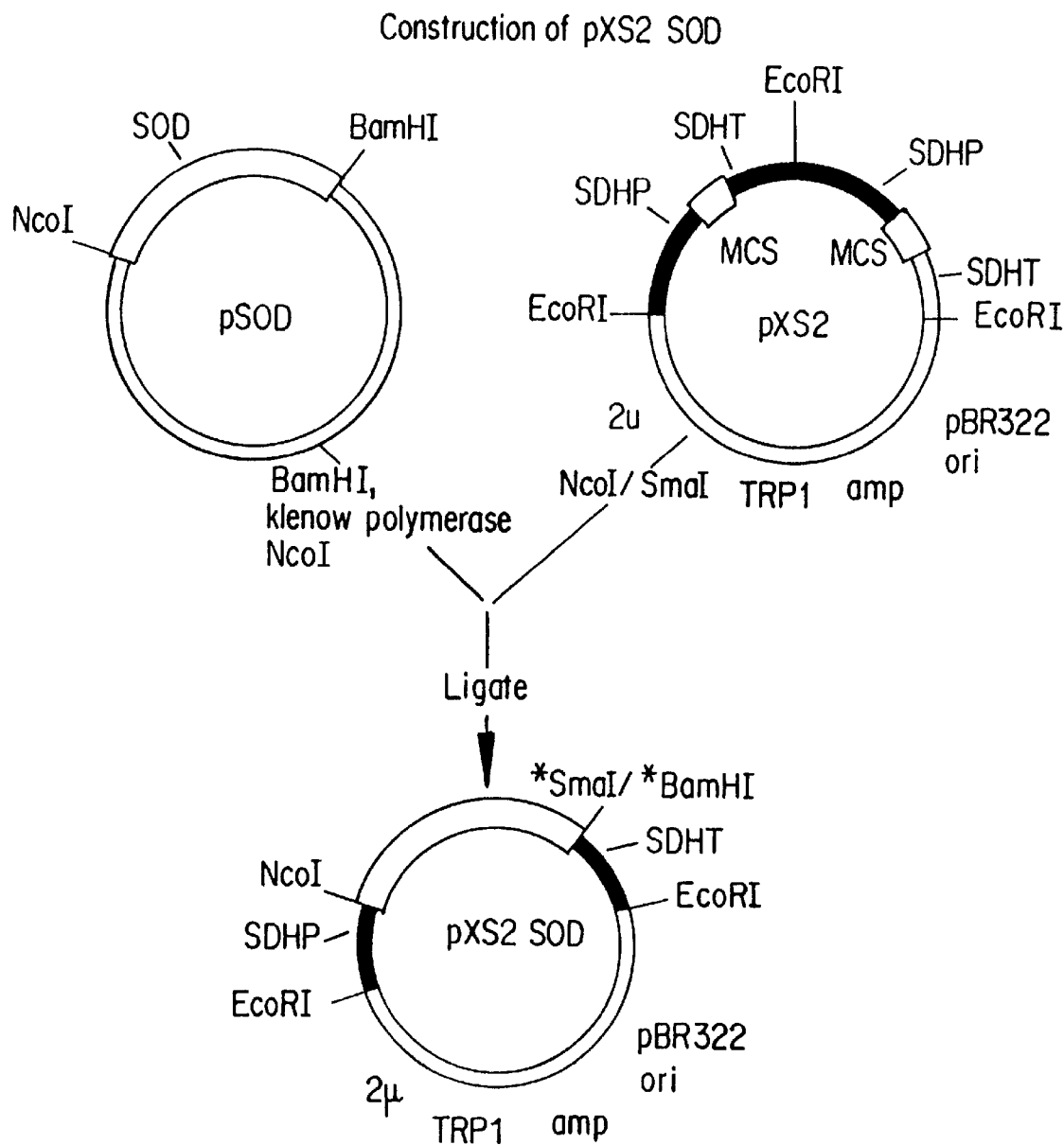
FIG. 5 is a schematic representation illustrating the construction of pxS2-SOD and pxS4 linker SOD.
Figure 5B:
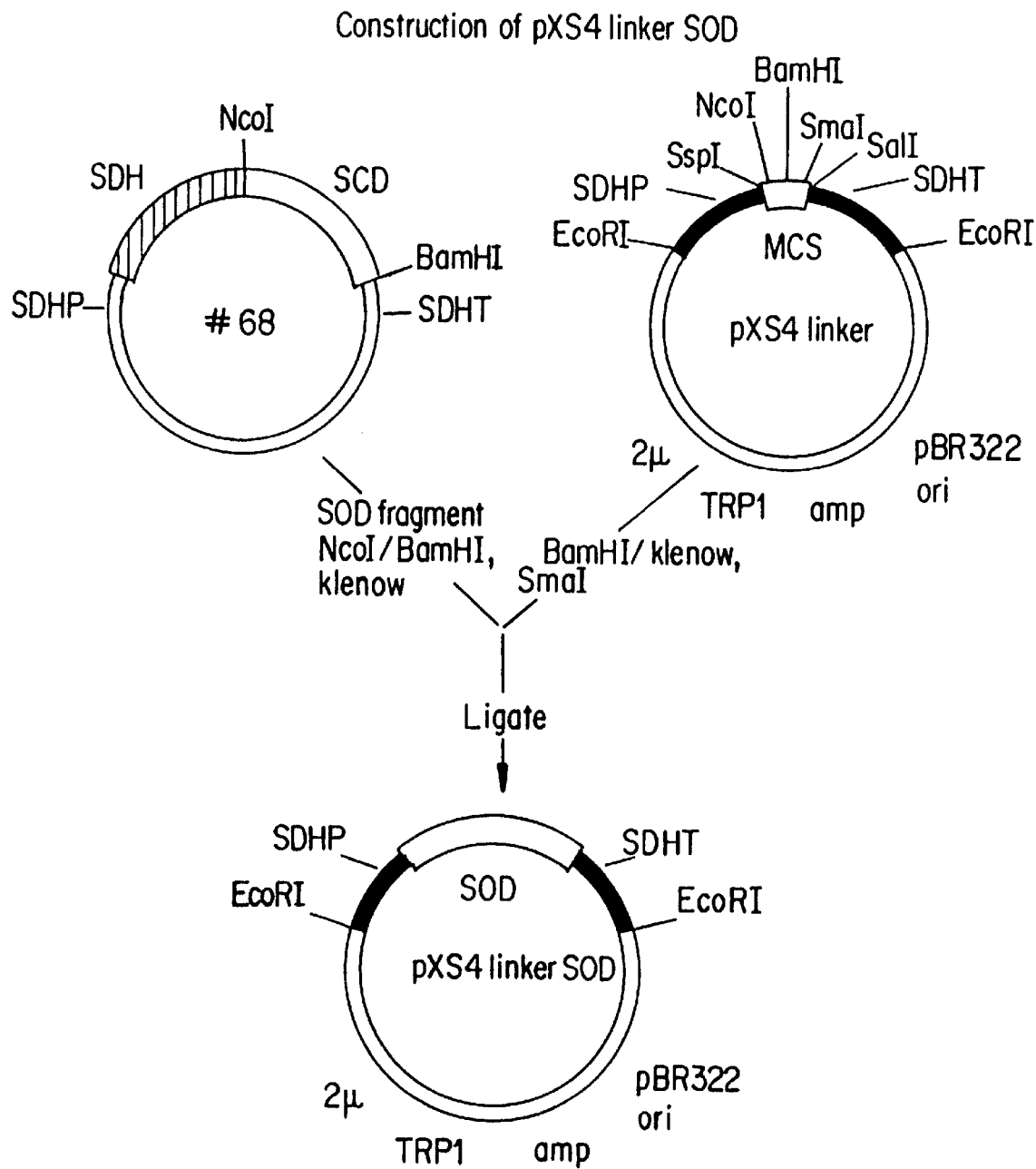

The source of the DNA coding for the human superoxide dismutase (SOD) gene was pSOD (obtained from J. Ostberg, M. Klass, Abbott Laboratories, Abbott Park, Ill.). The Applied Biosystem 340 synthesizer was used to synthesize seven separate oligonucieotides which were then assembled into the SOD gene using the Fok 1 method described by Mandecki et al. Gene, 94: 103 (1990). A 0.5 kb fragment containing the human SOD gene was excised from pSOD using restriction enzymes Bam HI and NcoI. Kilenow polymerase was used to blunt end the sticky ends generated by Bam HI. The fragment was ligated to pxS2 at the NcoI and SmaI sites and the ligation reaction transformed into E. coli strain TBI1. Transformants containing the SOD gene were identified by the restriction analysis of plasmid DNA extracted from several different transformants. Plasmids with SOD gene insert in the correct orientation were identified upon subsequent analysis with NcoI and EcoRV. Plasmid pxS2-SOD were identified as containing the SOD gene. (FIG. 5)
Step 2: SDS-PAGE Analysis of the Expression of Human Superoxide Dismutase Polypentide in 8000-8B LAG Transformed with pxS2-SOD.

Figure 6:
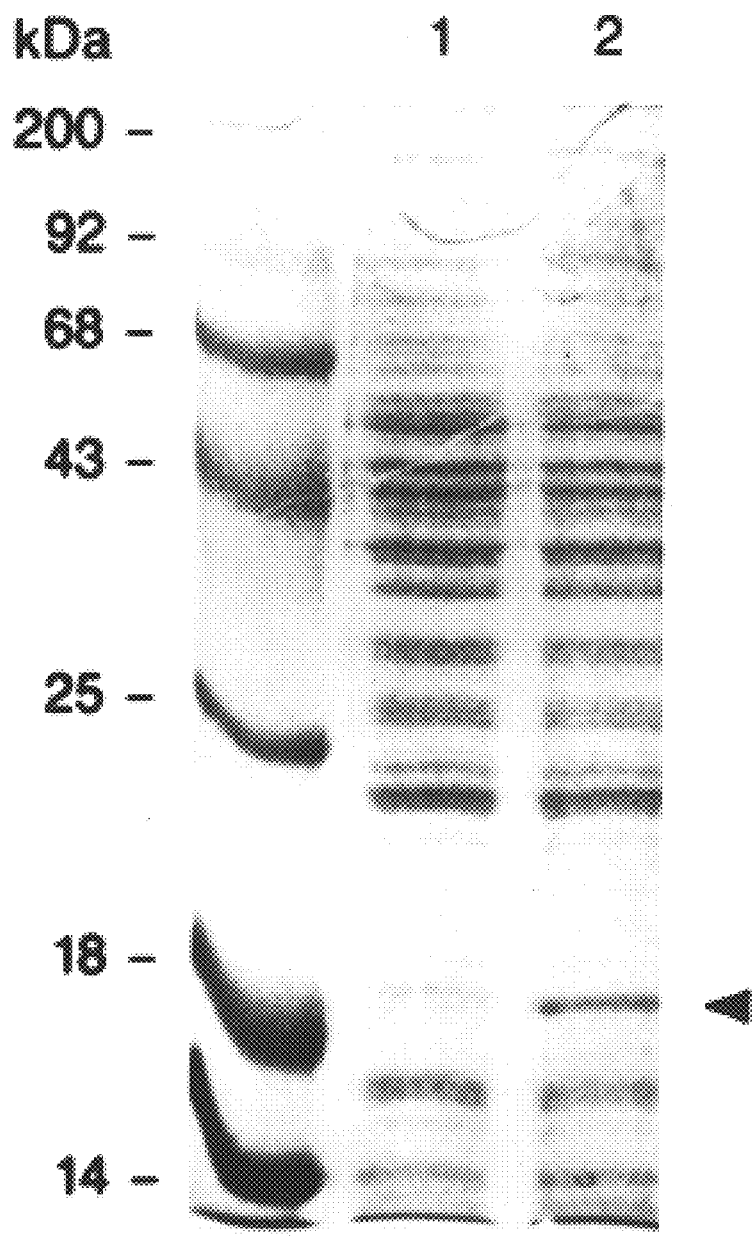
FIG. 6 illustrates the expression of unflised human superoltde dismutase polypeptide in yeast transformed with pxS2-SOD. Expression of human SOD polypeptide was determined visually by staining with Coomassie Blue. Lane 1 contains high Molecular weight protein markers from Bio-Rad. Lanes 2,3 contain extracts from 8000-8B transformants containing pxS4 and pxS2-SOD respectively.

Plasmids pxS4 and pxS2-SOD were transformed into S. cerevisiae 8000-8B LAG prepared as described above. The transformants were isolated in medium lacking tryptophan. Individual isolate of pxS4, pxS2-SOD was inoculated into 10 mls YNB liquid medium containing 2% sorbitol, 0.5% glucose, 25 mM $CuSO_4$, 25 mM $ZnSO_4$. A 200 microliter aliquot of saturated cultures were inoculated into 25 mls YNB liquid medium containing 2% sorbitol, 0.3% glucose, 25 mM $CuSO_4$, 25 mM $ZnSO_4$ and incubated at 30° C. Cell lysates from 10 mls of these cultures were further processed as described above. SDS analysis of the unfused superoxide dismutase is shown in FIG. 6. The results indicated a prominent polypeptide band that migrated as a 20 kilodalton polypeptide. Densitometric analysis of the gel determined that the human superoxide dismutase polypeptide was being expressed at 6% of the total soluble yeast polypeptide.

Example 7
Expression of Human Superoxide Dismutase (SOD) Polypentide from Yeast Expression Vector DXS4 Linker.
Sten 1: Construction of pXS4 Linker SOD.

A chemically synthesized superoxide dismutase gene was provided by J. Ostberg and M. Klass (Abbott Laboratories, Abbott Park, Ill.). Clone pS30 contains ~4.5 Kb yeast genomic fragment which codes for the entire yeast SDH gene. An NcoI fragment from pS30 containing approximately two thirds of the SDH gene was inserted into the unique NcoI site of plasmid pSOD which contains the chemically synthesized human superoxide dismutase gene. Restriction digestion with PstI was used to identify clone #68 which codes for a fusion of superoxide dismutase polypeptide with human SOD. This plasmid was used as a source of DNA for the human superoxide dismutase gene.

A 0.5 kb NcoI/BamHI fragment from clone #68 was isolated and treated with Klenow polymerase to fill in the sticky ends. This fragment was ligated to pXS4 linker which was previously blunt ended with Klenow polymerase at the SmaI and BamHI sites. DNA from several candidate clones was isolated and checked for the presence of the SOD gene by restriction analysis with BamHI and SalI. Clone pXS4 linker SOD contained the SOD gene in the correct orientation.
Step 2: Analysis of Expression of Human Superoxide Dismutase Polypeptide in Yeast Strain 8000-8B LAG. Transformed with pXS4 Linker-SOD, The transformation protocol of Percival et al., supra, was used to introduce pXS4 linker and pXS4 linker SOD into 8000-8B LAG. Transformants were isolated under tryptophan selection which selects for the plasmid. Individual transformants were repurified on YNB minimal medium lacking tryptophan.

Figure 7:
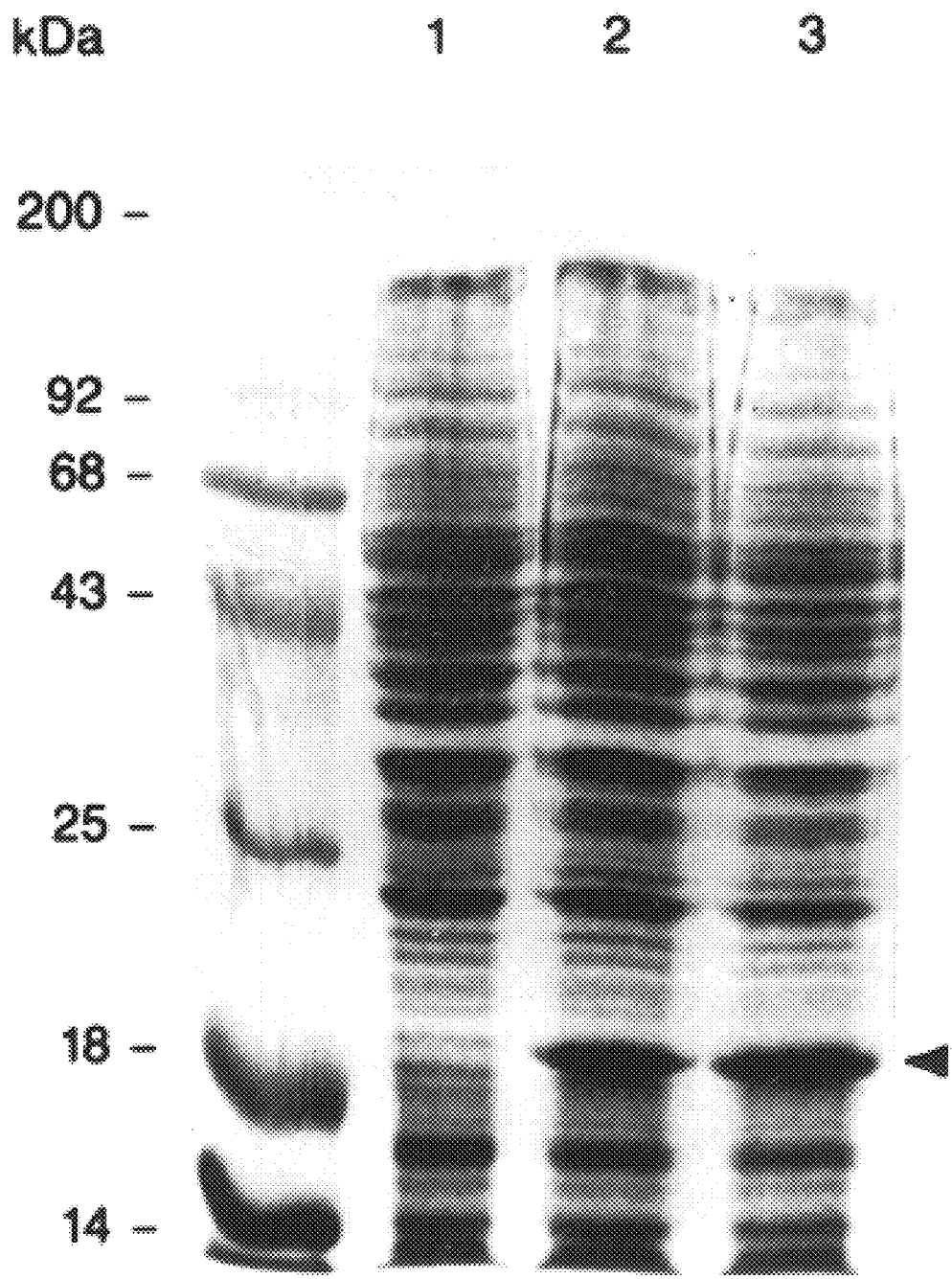
FIG. 7 illustrates the SDS-PAGE analysis of the expression of fused human superoxide dismutase polypeptide in transformants containing pxS4 linker SOD. The gel was stained with Coomiassie Blue. Lane 2 contains extracts from transformant containing the yeast expression vector pxS4 linker. Two individual transformants containing the human SOD gene in pxS4 linker were electrophoresed in lanes 3,4. High molecular weight protein standard supplied by Bio RAD was loaded in lane 1.

Transformants containing the two different plasmids were grown under tryptophan selection in 10 mls YNB liquid medium containing 2% sorbitol and 25 mM each of CuSO4 and $ZnSO_4$. Cells were incubated at 30° C. for 48 hours. Cell pellets were washed with 3 mls. distilled water, resuspended in 0.5 mL extraction buffer (0.05 M $KPO_4$ pH 7.4, 2 mM, b-mercapto-ethanol 1 mM PMSF) and vortexed with glass beads for 2 minutes. An equal volume of the extract was mixed with lysis buffer, boiled for 3 minutes and an aliquot of the extract was electrophoresed on SDS polyacrylamide gel which was then stained with Coomassie Blue. The data is presented in FIG. 7 which demonstrates a predominant polypeptide band that migrates with a molecular weight of 20 k daltons. Scans of the gels indicated that expression levels as high as 15% were achieved in 8000-B LAG expressing the human SOD polypeptide as a fusion with the yeast sorbitol$_{13}$ dehydrogenase polypeptide.

It will be appreciated by those skilled in the art that of the embodiments of the present invention are applicable to other types of heterologous polypeptides and are intended as examples rather than limitations. Accordingly, the description of the invention is not intended to limit the invention of the particular embodiments disclosed, but it is intended to encompass all equivalents and subject matter within the spirit and scope of the invention as described above as and set forth in the following claims.

What is claimed is:

1. A method of producing a heterologous polypeptide in *Saccharomyces cerevisiae*, said method comprising the steps of:
   (a) constructing a vector, replicable in *Saccharomyces cerevisiae*, comprising a regulatory nucleotide segment from *Saccharomyces cerevisiae* sorbitol dehydrogenase gene, which is induced by sorbitol, operably linked to a gene which encodes said heterologous polypeptide, wherein said regulatory nucleotide segment comprises a promoter and a terminator of said sorbital dehydrogenase gene;
   (b) introducing said vector into said *Saccharomyces cerevisiae*; and
   (c) producing said polypeptide under inducing conditions.

2. The method of claim 1 wherein the regulatory nucleotide segment further comprises the DNA sequence coding for the N-terminal eleven amino acid residues of the sorbitol dehydrogenase polypeptide.

3. The method of claim 2 wherein the regulatory nucleotide segment includes nucleic acid numbers 1–771 and nucleic acid numbers 1848–2760 of the nucleotide sequence (SEQ ID NO:1) shown in FIG. 1.

4. The method of claim 1 wherein the DNA regulatory sequence further includes nucleic acid numbers 772–805 of FIG. 1.

* * * * *